United States Patent

Araki et al.

Patent Number: 5,977,376
Date of Patent: Nov. 2, 1999

[54] HERBICIDAL 2-BENZOYLCYCLOHEXANE-1,3-DIONES AND RELATED COMPOUNDS

[75] Inventors: Kouichi Araki, Ibaraki-ken; Takako Brett, Tokyo; Kei Domom, Ibaraki; Atsushi Go, Ibaraki-ken; Masahito Ito, Ibaraki-ken; Hideshi Mukaida, Ibaraki-ken; Yukiko Oe, Ibaraki-ken, all of Japan

[73] Assignee: Rhone-Poulenc Agriculture Limited, Ongar, United Kingdom

[21] Appl. No.: 09/118,367

[22] Filed: Jul. 17, 1998

Related U.S. Application Data

[60] Provisional application No. 60/066,934, Nov. 17, 1997.

[30] Foreign Application Priority Data

Jul. 18, 1997 [GB] United Kingdom ................. 97 15162

[51] Int. Cl.⁶ ..................... C07D 249/08; C07D 233/54; C07D 233/60; A01N 43/80
[52] U.S. Cl. ..................... 548/268.6; 504/139; 504/272; 504/261; 504/275; 504/276; 504/280; 548/253; 548/310.1; 548/341.1; 548/341.5; 548/376.1; 548/377.1
[58] Field of Search ................. 548/268.6, 253, 548/341.5, 341.1, 310.1, 376.1, 371.1; 504/139, 261, 272, 275, 276, 280

[56] References Cited

U.S. PATENT DOCUMENTS

| | | | |
|---|---|---|---|
| 4,780,127 | 10/1988 | Michaely et al. | 504/349 X |
| 4,822,906 | 4/1989 | Carter | 558/416 |
| 5,006,148 | 4/1991 | Fischer et al. | 71/72 |
| 5,536,703 | 7/1996 | Lee | 504/349 |
| 5,554,540 | 9/1996 | Fischer et al. | 504/281 |
| 5,559,218 | 9/1996 | Kast et al. | 534/850 |

FOREIGN PATENT DOCUMENTS

| | | |
|---|---|---|
| 0370332 | 5/1990 | European Pat. Off. |
| 0666254 | 8/1995 | European Pat. Off. |
| 91/19709 | 12/1991 | WIPO |
| 96/26192 | 2/1996 | WIPO |

*Primary Examiner*—Floyd D. Higel
*Attorney, Agent, or Firm*—Burns, Doanne, Swecker & Mathis, L.L.P.

[57] ABSTRACT

The invention relates to compounds of formula (I):

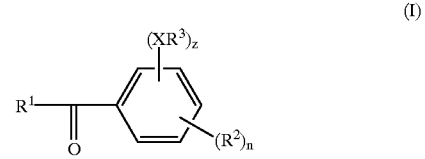

and to their use as herbicides.

35 Claims, No Drawings

HERBICIDAL 2-BENZOYLCYCLOHEXANE-1,3-DIONES AND RELATED COMPOUNDS

CROSS-REFERENCE TO RELATED APPLICATION

This application claims the priority of copending U.S. Provisional Patent Application No. 60/066,934, filed Nov. 17, 1997, incorporated by reference herein in its entirety and relied upon.

CROSS-REFERENCE TO PRIORITY APPLICATION

This application claims priority under 35 U.S.C. § 119 of UK Patent Application No. 97 15162.5, filed Jul. 18, 1997, incorporated by reference herein in its entirety and relied upon.

This invention relates to novel 2-benzoylcyclohexane-1,3-dione and related derivatives, compositions containing them, processes for their preparation, intermediates in their preparation and their use as herbicides.

Herbicidal 2-benzoylcyclohexane-1,3-diones are described in U.S. Pat. Nos. 4,780,127 and 5,536,703, and WO 96 26192 as well as EP 0666254, amongst other references. However none of the above publications disclose or suggest the presence of an aromatic heterocyclic ring linked by a ring nitrogen atom (optionally via a methylene) to the benzoyl ring.

The present invention provides 2-benzoylcyclohexane-1,3-dione derivatives of formula (I):

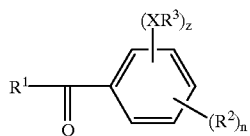
(I)

wherein:

$R^1$ represents a group of formula (II), (III), (IV) or (V):

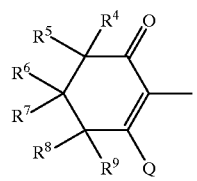
(II)

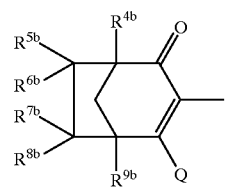
(III)

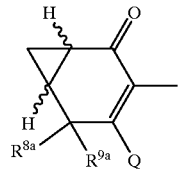
(IV)

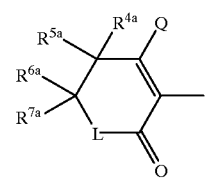
(V)

or a corresponding formula (IVa) or (Va):

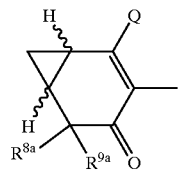
(IVa)

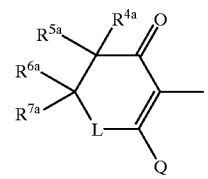
(Va)

in which the position of the carbonyl group and the group Q are reversed and the double bond in the ring is attached to the carbon atom attached to the group Q;

$R^2$ represents:

halogen:

lower alkyl which is optionally substituted by one or more halogen or —$OR^{10}$ a cycloalkyl group containing from three to six carbon atoms: or a group selected from nitro, cyano. —$CO_2R^{10}$, —$NR^{10}R^{11}$, —$S(O)_pR^{12}$, —$O(CH_2)_m OR^{10}$, —$COR^{10}$, —$N(R^{13})SO_2R^{12}$, —$OR^{12}$, —OH, —$OSO_2R^{12}$, —$(CR^{14}R^{15})_rS(O)_pR^{12}$, —$CONR^{10}R^{11}$, —$N(R^{1f})$—$C(Z)$=Y, —$C(R^{14}R^{15})NR^{13}R^{16}$, —$CH_2P(O)R^{10a}R^{10b}$, $R^{17}$, $SF_5$ and benzyl optionally substituted by from one to five groups $R^{18}$ which may be the same or different:

or two groups $R^2$, together with adjacent carbon atoms of the phenyl ring form a second phenyl ring or a 5- or 6-membered saturated or unsaturated heterocyclic ring which is fused to the first ring and contains one or two oxygen or sulphur atoms and is optionally substituted by one or more halogen, lower alkyl, lower haloalkyl or lower alkoxy groups, or one of the ring carbon atoms of the heterocyclic ring forms part of a carbonyl group or an oxime or lower alkoxyimine derivative thereof; (examples of the optionally substituted fused ring systems when formed include thiochroman, chroman, 2H-thiochromene, 2H-chromene, 4H-thiochromene, 4H-chromene, isothiochroman, isochroman, isothiochromene, isochromene, 1,3-benzodithiole, 1,3-benzodioxole, 1,3-benzoxathiole, 1,4-benzodithlin, 1,4-benzoxathiin. 1,4-benzoxathian, 13-benzoxathian, 3,1-benzoxathian and 1,3-benzodithian);

n represents zero or an integer from one to three; where n is greater than one the groups $R^2$ may be the same or different;

m represents one, two or three;

p and q represent zero, one or two;

t represents one, two, three or four (preferably one); when t is more than one $R^{14}$ and $R^{15}$ may be the same or different;

X represents $-(CR^{14}R^{15})_v-$;

v represents zero or one, $R^3$ represents a 5-membered heteroaromatic ring of formula (VI)

(VI)

in which D, E, G and J independently represent $CR^{19}$ or a nitrogen atom, with at least one of D, E, G and J representing $CR^{19}$ (when more than one $CR^{19}$ group is present they may be the same or different); or two adjacent groups may form a phenyl or a 5- to 7-membered heteroaromatic ring, which is fused to the first ring and is optionally substituted by one or more groups $R^{20}$, and when present the 5- to 7-membered heterocyclic ring may contain from one to four heteroatoms in the ring which may be the same or different selected from nitrogen, oxygen and sulphur;

z represents one or two; when z represents two the $-XR^3$ groups may be the same or different.

Q represents hydroxy, lower alkoxy, $OR^{21}$, $SR^{21}$ or $SR^{22}$;

L represents oxygen or $NR^{14}$;

$R^4$, $R^{4a}$, $R^{4b}$, $R^5$, $R^{5a}$, $R^{5b}$, $R^6$, $R^{6a}$, $R^{6b}$, $R^7$, $R^{7a}$, $R^{7b}$, $R^8$, $R^{8a}$, $R^{8b}$, $R^9$, $R^{9a}$ and $R^{9b}$ represent the same or different groups selected from hydrogen, $R^{17}$, $-(CH_2)_uCO_2R^{14}$, halogen, cyano, lower alkoxy, $-(CH_2)_x$-[phenyl optionally substituted by from one to five groups $R^{18}$ which may be the same or different], and cycloalkyl containing from three to six carbon atoms optionally substituted by lower alkyl or $-S(O)_pR^{22}$;

u represents zero, one or two;

x represents zero or one;

$R^{10}$ and $R^{11}$ which may be the same or different, each represents hydrogen or $R^{17}$;

$R^{10a}$ and $R^{10b}$ which may be the same or different, each represents lower alkyl or lower alkoxy;

$R^{12}$ represents:

$R^{17}$; or a cycloalkyl group containing from three to six carbon atoms; or a group $-(CH_2)_w$-[phenyl optionally substituted by from one to five groups $R^{18}$ which may be the same or different];

w represents zero or one;

$R^{13}$ represents:

hydrogen, $R^{12}$ or $OR^{22}$:

$R^{14}$ and $R^{15}$ independently represent hydrogen, lower alkyl or lower haloalkyl (preferably containing up to three carbon atoms);

$R^{16}$ represents $-SO_2R^{12}$ or $-C(Z)=Y$;

$R^{17}$ represents:

lower alkyl, lower haloalkyl, lower alkenyl, lower haloalkenyl, lower alkynyl or lower haloalkynyl;

$R^{18}$ represents a group selected from halogen, $R^{23}$, nitro, cyano, $-CO_2R^{10}$, $-S(O)_pR^{22}$, $-OR^{22}$ and $-NR^{10}R^{11}$;

$R^{19}$ represents:

a group selected from hydrogen, halogen, $R^{23}$, nitro, cyano, $-CO_2R^{10}$, $-S(O)_pR^{22}$, $-OR^{22}$, $-NR^{10}R^{11}$ and cyclopropyl;

$R^{20}$ represents halogen or $R^{17}$;

$R^{21}$ represents phenyl optionally substituted by from one to five groups selected from halogen, lower alkyl, lower haloalkyl, lower alkoxy and nitro;

$R^{22}$ represents lower alkyl or lower haloalkyl;

$R^{23}$ represents a straight- or branched-chain alkyl group containing one to three carbon atoms optionally substituted by one or more halogen atoms;

Y is oxygen or sulphur (preferably Y represents oxygen);

Z represents a group selected from $R^{17}$, $-NR^{24}R^{25}$, $-SR^{12}$ and $-OR^{12}$;

$R^{24}$ and $R^{25}$ independently represent hydrogen or $R^{12}$;

and agriculturally acceptable salts and metal complexes thereof, which possess valuable herbicidal properties.

Compounds of formula (I) may exist in enolic tautomeric forms that may give rise to geometric isomers around the enolic double bond. Furthermore in certain cases the above substituents may contribute to optical isomerism and/or stereoisomerism. All such forms and mixtures are embraced by the present invention.

It is to be understood that in this specification compounds comprising a cyclohexane ring corresponding to formula (IV) or (V) or a precursor thereof include the compounds with the corresponding formula (IVa) or (Va) or precursors thereof.

In the description unless otherwise specified the following terms are generally defined thus:

'lower alkyl' means a straight- or branched-chain alkyl group having one to six carbon atoms;

'lower haloalkyl' means a straight- or branched-chain alkyl group having one to six carbon atoms, substituted by one or more halogens;

'lower alkoxy' means a straight- or branched-chain alkoxy group having one to six carbon atoms;

'lower haloalkoxy' means a straight- or branched-chain alkoxy group having one to six carbon atoms, substituted by one or more halogens;

'lower alkenyl' means a straight- or branched-chain alkenyl group having two to six carbon atoms;

'lower haloalkenyl' means a straight- or branched-chain alkenyl group having two to six carbon atoms, substituted by one or more halogens;

'lower alkynyl' means a straight- or branched-chain alkynyl group having three to six carbon atoms;

'lower haloalkynyl' means a straight- or branched-chain alkynyl group having three to six carbon atoms, substituted by one or more halogens;

'halogen' means a fluorine, chlorine, bromine or iodine atom.

By the term "agriculturally acceptable salts" is meant salts the cations or anions of which are known and accepted in the art for the formation of salts for agricultural or horticultural use. Preferably the salts are water-soluble. Suitable salts with bases include alkali metal (eg. sodium and potassium), alkaline earth metal (eg. calcium and magnesium), ammonium and amine (eg. diethanolamine, triethanolamine, octylamine, morpholine and dioctylmethylamine) salts. Suitable acid addition salts, formed by compounds of formula (I) containing an amino group, include salts with inorganic acids, for example hydrochlorides, sulphates, phosphates and nitrates and salts with organic acids, for example acetic acid.

By the term "metal complexes" is meant compounds wherein Q represents hydrogen (or a tautomer thereof) in which one or more of the oxygen atoms of the 2-benzoylcyclohexane-1,3-dione derivatives of formula (I) act as chelating agents to a metal cation. Examples of such cations include zinc, manganese, cupric, cuprous, ferric, ferrous, titanium and aluminium.

The compounds of the invention, in certain aspects of their properties, for example their high levels of herbicidal activity, show advantageous properties over known compounds.

Compounds wherein one $XR^3$ group is present are preferred (preferably the $XR^3$ group is at the 2- or 4-position of the phenyl ring).

Compounds wherein X represents $-(CH_2)_v-$ are preferred (compounds in which v represents zero are especially preferred).

Compounds wherein Q represents hydroxy or —S-phenyl are preferred (compounds in which Q represents hydroxy are especially preferred).

Compounds of formula (I) in which the 2- and 4-positions of phenyl are substituted are also preferred.

Preferably $R^3$ is selected from pyrazol-1-yl, imidazol-1-yl, 1,2,4-triazol-1-yl, 1,2,3-triazol-1-yl, 1,2,3-triazol-2-yl, 1,2,3,4-tetrazol-1-yl and benzimidazol-1-yl (1,2,3-triazol-1-yl, 1,2,3-triazol-2-yl are more preferred, and 1,2,4-triazol- 1 -yl is most preferred).

Preferably $R^3$ is a ring of formula (VI) wherein $R^{19}$ represents hydrogen, halogen or $R^{23}$.

In formula (I) above, preferably the 5- and 6-positions of phenyl are unsubstituted.

Preferably $R^1$ represents a group of formula (II).

Preferably $R^2$ represents halogen, a straight- or branched-chain alkyl group containing up to four carbon atoms optionally substituted by one or more halogen atoms; or a group selected from nitro, cyano, $-S(O)_pR^{12}$, $-OR^{12}$, $-CH_2S(O)_qR^{12}$ wherein $R^{12}$ represents lower alkyl or lower haloalkyl; or benzyl optionally substituted by $-S(O)_p R^{22}$ wherein $R^{22}$ represents lower alkyl; or two groups $R^2$ together with adjacent carbon atoms of the phenyl ring form a second phenyl ring.

Preferably n represents one or two.

A preferred class of compounds of formula (I) above are those wherein:

$R^1$ is selected from:
a group of formula (II) wherein $R^4$, $R^5$, $R^6$, $R^7$, $R^8$ and $R^9$ represent hydrogen or lower alkyl; or
a group of formula (III) wherein $R^{4b}$, $R^{5b}$, $R^{6b}$, $R^{7b}$, $R^{8b}$ and $R^{9b}$ represent hydrogen or lower alkyl; or
a group of formula (IV) wherein $R^{8a}$ and $R^{9a}$ represent hydrogen or lower alkyl; and
a group of formula (V) wherein $R^{4a}$, $R^{5a}$, $R^{6a}$ and $R^{7a}$ represent hydrogen or lower alkyl, and L represents NH;
Q represents hydroxy or —S-phenyl;
$R^2$ represents:
a straight- or branched-chain alkyl group containing up to three carbon atoms optionally substituted by one or more halogen atoms; or a group selected from halogen, nitro, $-S(O)_pR^{12}$, $-OR^{12}$, $-CH_2S(O)_qR^{12}$, $-CH_2NR^{13}R^{16}$, $-N(R^{13})SO_2R^{12}$, $-N(R^{13})CO_2R^{12}$ and benzyl optionally substituted by $-S(O)_pR^{22}$;
n represents zero, one or two;
X represents $-(CH_2)_v-$;
$R^3$ represents a 5-membered heteroaromatic ring of formula (VI) which is selected from pyrazol-1-yl, imidazol-1-yl, 1,2,4-triazol-1-yl, 1,2,3-triazol-1-yl, 1,2,3-triazol-2-yl, 1,2,3,4-tetrazol-1 -yl and benzimidazol-1-yl, the ring systems of which are substituted by one or two $R^{19}$ groups;
z represents one;
$R^{12}$ and $R^{13}$ independently represent lower alkyl or lower haloalkyl;
$R^{16}$ represents $-SO_2R^{12}$ or $CO_2R^{12}$;

$R^{19}$ represents hydrogen or a straight- or branched-chain alkyl group containing up to three carbon atoms; and
$R^{22}$ represents lower alkyl.

A particularly preferred class of compounds of formula (I) above are those wherein:
$R^1$ is selected from:
to a group of formula (II) wherein $R^4$, $R^5$, $R^6$, $R^7$, $R^8$ and $R^9$ represent hydrogen, methyl or ethyl; or
a group of formula (III) wherein $R^{4b}$, $R^{5b}$, $R^{6b}$, $R^{7b}$, $R^{8b}$ and $R^{9b}$ represent hydrogen, methyl or ethyl: or
a group of formula (IV) wherein $R^{8a}$ and $R^{9a}$ represent hydrogen, methyl or ethyl; and
a group of formula (V) wherein $R^{4a}$, $R^{5a}$, $R^{6a}$ and $R^{7a}$ represent hydrogen, methyl or ethyl, and L represents NH;
Q represents hydroxy or —S-phenyl,
$R^2$ represents:
halogen, a straight- or branched-chain alkyl group containing up to three carbon atoms optionally substituted by one or more halogen atoms; or a group selected from $-S(O)_pCH_3$, $-CH_2S(O)_qCH_3$, $-OCH_3$ and benzyl optionally substituted by $-S(O)_pCH_3$;
X represents a bond;
$R^3$ represents a pyrazol-1-yl, imidazol-1-yl, 1,2,3-triazol-1-yl, 1,2,3 -triazol-2-yl, 1,2,4-triazol-1-yl or 1,2,3,4-tetrazol-1-yl ring substituted by one or two $R^{19}$ groups, wherein $R^{19}$ represents hydrogen, halogen or optionally halogenated methyl;
z represents one; and
n represents 0, 1 or 2.

A further particularly preferred class of compounds of formula (I) above are those wherein:
$R^1$ represents a group of formula (II) wherein $R^4$, $R^5$, $R^6$, $R^7$, $R^8$ and $R^9$ represent hydrogen, methyl or ethyl;
Q represents hydroxy or —S-phenyl;
$R^2$ represents:
halogen, a straight- or branched- chain alkyl group containing up to three carbon atoms optionally substituted by one or more halogen atoms; or a group selected from $-S(O)_pCH_3$, $-CH_2S(O)_qCH_3$, $-OCH_3$ and benzyl optionally substituted by $-S(O)_pCH_3$;
X represents a bond;
$R^3$ represents a pyrazol-1-yl, imidazol-1-yl, 1,2,3-triazol-1-yl, 1,2,3-triazol-2-yl, 1,2,4-triazol-1-yl or 1,2,3,4-tetrazol-1-yl ring substituted by one or two $R^{19}$ groups, wherein $R^{19}$ represents hydrogen, halogen or optionally halogenated methyl;
z represents one; and
n represents 0, 1 or 2.

A further particularly preferred class of compounds of formula (I) above are those wherein:
$R^1$ represents a formula (II) wherein wherein $R^4$, $R^5$, $R^8$ and $R^9$ represent hydrogen;
$R^6$ and $R^7$ represent hydrogen or methyl;
$R^2$ represents:
optionally halogenated methyl;
Q represents hydroxy or —S-phenyl;
X represents a bond;
$R^3$ represents a 1,2,4-triazol-1-yl ring; and
z and n represent one.

Particularly preferred compounds of the invention include:
2-[4-(1,2,4-triazol-1-yl)-2-trifluoromethylbenzoyl]cyclohexane-1,3-dione (Compound 1);
3-phenylthio-2-[4-(1,2,4-triazol-1-yl)-2-trifluoromethylbenzoyl]cyclohex-2-ene-1-one (Compound 2); and
5,5-dimethyl-2-[4-(1,2,4-triazol-1-yl)-2-trifluoromethylbenzoyl]cyclohexane-1,3-dione (Compound 3)

2-[2-chloro-4-(1,2,4-triazol-1-yl)benzoyl]cyclohexane-1,3-dione (Compound 31)

2-[2-methyl-4-(1,2,4-triazol-1-yl)benzoyl]cyclohexane-1,3-dione (Compound 32)

2-[2-methylthio-4-(1,2,4-triazol-1-yl)benzoyl]cyclohexane-1,3-dione (Compound 42)

5-methyl-2-[4-(1,2,4-triazol-1-yl)-2-trifluoromethylbenzoyl]cyclohexane-1,3-dione (Compound 88)

5-methyl-2-[2-chloro-4-(1,2,4-triazol-1-yl)benzoyl]cyclohexane-1,3-dione (Compound 99)

5,5-dimethyl-2-[2-chloro-4-(1,2,4-triazol-1-yl)benzoyl]cyclohexane-1,3-dione (Compound 166).

The following compounds of formula (1) in which $R^1$ represents a group of formula (II); $R^4$, $R^5$, $R^8$ and $R^9$ represent hydrogen, and the group $(XR^3)_z$ is attached either to the 4-position of the phenyl ring Table 1), or to the 2-position of the phenyl ring (Table 2), or to the 3-position of the phenyl ring (Table 3), form part of the present invention. In the Tables that follow, Me means methyl, Et means ethyl, Pr means propyl, and Ph means phenyl. Where subscripts do not appear in the Tables it will be understood that in appropriate cases they are present (e.g. CF3 means $CF_3$ etc.).

TABLE 1

| Cpd No. | R6 | R7 | Q | (R2)n | (XR3)z |
|---|---|---|---|---|---|
| 1 | H | H | OH | 2-CF3 | 1,2,4-triazol-1-yl |
| 2 | H | H | SPh | 2-CF3 | 1,2,4-triazol-1-yl |
| 3 | Me | Me | OH | 2-CF3 | 1,2,4-triazol-1-yl |
| 4 | H | H | OH | 2-CF3 | 1,2,3-triazol-1-yl |
| 5 | H | H | OH | 2-CH2SMe | 1,2,3-triazol-1-yl |
| 6 | H | H | OH | 2-Cl | 1,2,3-triazol-1-yl |
| 7 | H | H | OH | 2-Me | 1,2,3-triazol-1-yl |
| 8 | H | H | OH | 2-SMe | 1,2,3-triazol-1-yl |
| 9 | H | H | OH | 2-SMe-3-Br | 1,2,3-triazol-1-yl |
| 10 | H | H | OH | 2-SMe-3-F | 1,2,3-triazol-1-yl |
| 11 | H | H | OH | 2-SMe-3-SMe | 1,2,3-triazol-1-yl |
| 12 | H | H | OH | 2-CF3 | 1,2,3-triazol-2-yl |
| 13 | H | H | OH | 2-CH2SMe | 1,2,3-triazol-2-yl |
| 14 | H | H | OH | 2-Cl | 1,2,3-triazol-2-yl |
| 15 | H | H | OH | 2-Me | 1,2,3-triazol-2-yl |
| 16 | H | H | OH | 2-SMe | 1,2,3-triazol-2-yl |
| 17 | H | H | OH | 2-SMe-3-Br | 1,2,3-triazol-2-yl |
| 18 | H | H | OH | 2-SMe-3-F | 1,2,3-triazol-2-yl |
| 19 | H | H | OH | 2-SMe-3-SMe | 1,2,3-triazol-2-yl |
| 20 | H | H | OH | 2-Br | 1,2,4-triazol-1-yl |
| 21 | H | H | OH | 2-CH2[(2-MeS)Ph] | 1,2,4-triazol-1-yl |
| 22 | H | H | OH | 2-CH2[(2-MeSO)Ph] | 1,2,4-triazol-1-yl |
| 23 | H | H | OH | 2-CH2[(2-MeSO2)Ph] | 1,2,4-triazol-1-yl |
| 24 | H | H | OH | 2-CH2N(Me)CO2Me | 1,2,4-triazol-1-yl |
| 25 | H | H | OH | 2-CH2N(Me)SO2Me | 1,2,4-triazol-1-yl |
| 26 | H | H | OH | 2-CH2Ph | 1,2,4-triazol-1-yl |
| 27 | H | H | OH | 2-CH2SMe | 1,2,4-triazol-1-yl |
| 28 | H | H | OH | 2-CH2SMe | 1,2,4-triazol-1-yl |
| 29 | H | H | OH | 2-CH2SO2Me | 1,2,4-triazol-1-yl |
| 30 | H | H | OH | 2-CH2SOMe | 1,2,4-triazol-1-yl |
| 31 | H | H | OH | 2-Cl | 1,2,4-triazol-1-yl |
| 32 | H | H | OH | 2-Me | 1,2,4-triazol-1-yl |
| 33 | H | H | OH | 2-Me-3-SMe | 1,2,4-triazol-1-yl |
| 34 | H | H | OH | 2-Me-3-SO2Me | 1,2,4-triazol-1-yl |
| 35 | H | H | OH | 2-Me-3-SOMe | 1,2,4-triazol-1-yl |
| 36 | H | H | OH | 2-NMeCO2Me | 1,2,4-triazol-1-yl |
| 37 | H | H | OH | 2-NMeSO2Me | 1,2,4-triazol-1-yl |
| 38 | H | H | OH | 2-OMe | 1,2,4-triazol-1-yl |
| 39 | H | H | OH | 2-OMe-3-SMe | 1,2,4-triazol-1-yl |
| 40 | H | H | OH | 2-OMe-3-SO2Me | 1,2,4-triazol-1-yl |
| 41 | H | H | OH | 2-OMe-3-SOMe | 1,2,4-triazol-1-yl |
| 42 | H | H | OH | 2-SMe | 1,2,4-triazol-1-yl |
| 43 | H | H | OH | 2-SMe-3-Br | 1,2,4-triazol-1-yl |
| 44 | H | H | OH | 2-SMe-3-Cl | 1,2,4-triazol-1-yl |
| 45 | H | H | OH | 2-SMe-3-F | 1,2,4-triazol-1-yl |
| 46 | H | H | OH | 2-SMe-3-OMe | 1,2,4-triazol-1-yl |

TABLE 1-continued

| Cpd No. | R6 | R7 | Q | (R2)n | (XR3)z |
|---|---|---|---|---|---|
| 47 | H | H | OH | 2-SMe-3-SMe | 1,2,4-triazol-1-yl |
| 48 | H | H | OH | 2-SO2Me | 1,2,4-triazol-1-yl |
| 49 | H | H | OH | 2-SO2Me-3-Cl | 1,2,4-triazol-1-yl |
| 50 | H | H | OH | 2-SO2Me-3-OMe | 1,2,4-triazol-1-yl |
| 51 | H | H | OH | 2-SOMe | 1,2,4-triazol-1-yl |
| 52 | H | H | OH | 2-SOMe-3-Cl | 1,2,4-triazol-1-yl |
| 53 | H | H | OH | 2-SOMe-3-OMe | 1,2,4-triazol-1-yl |
| 54 | H | H | OH | 2-NO2 | 1,2,4-triazol-1-yl |
| 55 | H | H | OH | 2-CF3 | imidazol-1-yl |
| 56 | H | H | OH | 2-CH2SMe | imidazol-1-yl |
| 57 | H | H | OH | 2-Cl | imidazol-1-yl |
| 58 | H | H | OH | 2-Me | imidazol-1-yl |
| 59 | H | H | OH | 2-SMe | imidazol-1-yl |
| 60 | H | H | OH | 2-SMe-3-Br | imidazol-1-yl |
| 61 | H | H | OH | 2-SMe-3-F | imidazol-1-yl |
| 62 | H | H | OH | 2-SMe-3-SMe | imidazol-1-yl |
| 63 | H | H | OH | 2-CF3 | pyrazol-1-yl |
| 64 | H | H | OH | 2-CH2SMe | pyrazol-1-yl |
| 65 | H | H | OH | 2-Cl | pyrazol-1-yl |
| 66 | H | H | OH | 2-Me | pyrazol-1-yl |
| 67 | H | H | OH | 2-SMe | pyrazol-1-yl |
| 68 | H | H | OH | 2-CF3 | tetrazol-1-yl |
| 69 | H | H | OH | 2-SMe | tetrazol-1-yl |
| 70 | H | H | OH | 2-SMe-3-SMe | tetrazol-1-yl |
| 71 | H | Me | OH | 2-CF3 | 1,2,3-triazol-1-yl |
| 72 | H | Me | OH | 2-CH2SMe | 1,2,3-triazol-1-yl |
| 73 | H | Me | OH | 2-Cl | 1,2,3-triazol-1-yl |
| 74 | H | Me | OH | 2-Me | 1,2,3-triazol-1-yl |
| 75 | H | Me | OH | 2-SMe | 1,2,3-triazol-1-yl |
| 76 | H | Me | OH | 2-SMe-3-Br | 1,2,3-triazol-1-yl |
| 77 | H | Me | OH | 2-SMe-3-F | 1,2,3-triazol-1-yl |
| 78 | H | Me | OH | 2-SMe-3-SMe | 1,2,3-triazol-1-yl |
| 79 | H | Me | OH | 2-CF3 | 1,2,3-triazol-2-yl |
| 80 | H | Me | OH | 2-CH2SMe | 1,2,3-triazol-2-yl |
| 81 | H | Me | OH | 2-Cl | 1,2,3-triazol-2-yl |
| 82 | H | Me | OH | 2-Me | 1,2,3-triazol-2-yl |
| 83 | H | Me | OH | 2-SMe | 1,2,3-triazol-2-yl |
| 84 | H | Me | OH | 2-SMe-3-Br | 1,2,3-triazol-2-yl |
| 85 | H | Me | OH | 2-SMe-3-F | 1,2,3-triazol-2-yl |
| 86 | H | Me | OH | 2-SMe-3-SMe | 1,2,3-triazol-2-yl |
| 87 | H | Me | OH | 2-Br | 1,2,4-triazol-1-yl |
| 88 | H | Me | OH | 2-CF3 | 1,2,4-triazol-1-yl |
| 89 | H | Me | OH | 2-CH2[(2-MeS)Ph] | 1,2,4-triazol-1-yl |
| 90 | H | Me | OH | 2-CH2[(2-MeSO)Ph] | 1,2,4-triazol-1-yl |
| 91 | H | Me | OH | 2-CH2[(2-MeSO2)Ph] | 1,2,4-triazol-1-yl |
| 92 | H | Me | OH | 2-CH2N(Me)CO2Me | 1,2,4-triazol-1-yl |
| 93 | H | Me | OH | 2-CH2N(Me)SO2Me | 1,2,4-triazol-1-yl |
| 94 | H | Me | OH | 2-CH2Ph | 1,2,4-triazol-1-yl |
| 95 | H | Me | OH | 2-CH2SMe | 1,2,4-triazol-1-yl |
| 96 | H | Me | OH | 2-CH2SMe | 1,2,4-triazol-1-yl |
| 97 | H | Me | OH | 2-CH2SO2Me | 1,2,4-triazol-1-yl |
| 98 | H | Me | OH | 2-CH2SOMe | 1,2,4-triazol-1-yl |
| 99 | H | Me | OH | 2-Cl | 1,2,4-triazol-1-yl |
| 100 | H | Me | OH | 2-Me | 1,2,4-triazol-1-yl |
| 101 | H | Me | OH | 2-Me-3-SMe | 1,2,4-triazol-1-yl |
| 102 | H | Me | OH | 2-Me-3-SO2Me | 1,2,4-triazol-1-yl |
| 103 | H | Me | OH | 2-Me-3-SOMe | 1,2,4-triazol-1-yl |
| 104 | H | Me | OH | 2-NMeCO2Me | 1,2,4-triazol-1-yl |
| 105 | H | Me | OH | 2-NMeSO2Me | 1,2,4-triazol-1-yl |
| 106 | H | Me | OH | 2-OMe | 1,2,4-triazol-1-yl |
| 107 | H | Me | OH | 2-OMe-3-SMe | 1,2,4-triazol-1-yl |
| 108 | H | Me | OH | 2-OMe-3-SO2Me | 1,2,4-triazol-1-yl |
| 109 | H | Me | OH | 2-OMe-3-SOMe | 1,2,4-triazol-1-yl |
| 110 | H | Me | OH | 2-SMe | 1,2,4-triazol-1-yl |
| 111 | H | Me | OH | 2-SMe-3-Br | 1,2,4-triazol-1-yl |
| 112 | H | Me | OH | 2-SMe-3-Cl | 1,2,4-triazol-1-yl |
| 113 | H | Me | OH | 2-SMe-3-F | 1,2,4-triazol-1-yl |
| 114 | H | Me | OH | 2-SMe-3-OMe | 1,2,4-triazol-1-yl |
| 115 | H | Me | OH | 2-SMe-3-SMe | 1,2,4-triazol-1-yl |
| 116 | H | Me | OH | 2-SO2Me | 1,2,4-triazol-1-yl |
| 117 | H | Me | OH | 2-SO2Me-3-Cl | 1,2,4-triazol-1-yl |
| 118 | H | Me | OH | 2-SO2Me-3-OMe | 1,2,4-triazol-1-yl |
| 119 | H | Me | OH | 2-SOMe | 1,2,4-triazol-1-yl |
| 120 | H | Me | OH | 2-SOMe-3-Cl | 1,2,4-triazol-1-yl |
| 121 | H | Me | OH | 2-SOMe-3-OMe | 1,2,4-triazol-1-yl |
| 122 | H | Me | OH | 2-NO2 | 1,2,4-triazol-1-yl |

TABLE 1-continued

| Cpd No. | R6 | R7 | Q | (R2)n | (XR3)z |
|---|---|---|---|---|---|
| 123 | H | Me | OH | 2-CF3 | imidazol-1-yl |
| 124 | H | Me | OH | 2-CH2SMe | imidazol-1-yl |
| 125 | H | Me | OH | 2-Cl | imidazol-1-yl |
| 126 | H | Me | OH | 2-Me | imidazol-1-yl |
| 127 | H | Me | OH | 2-SMe | imidazol-1-yl |
| 128 | H | Me | OH | 2-SMe-3-Br | imidazol-1-yl |
| 129 | H | Me | OH | 2-SMe-3-F | imidazol-1-yl |
| 130 | H | Me | OH | 2-SMe-3-SMe | imidazol-1-yl |
| 131 | H | Me | OH | 2-CF3 | pyrazol-1-yl |
| 132 | H | Me | OH | 2-CH2SMe | pyrazol-1-yl |
| 133 | H | Me | OH | 2-Cl | pyrazol-1-yl |
| 134 | H | Me | OH | 2-Me | pyrazol-1-yl |
| 135 | H | Me | OH | 2-SMe | pyrazol-1-yl |
| 136 | H | Me | OH | 2-CF3 | tetrazol-1-yl |
| 137 | H | Me | OH | 2-SMe | tetrazol-1-yl |
| 138 | H | Me | OH | 2-SMe-3-SMe | tetrazol-1-yl |
| 139 | Me | Me | OH | 2-CF3 | 1,2,3-triazol-1-yl |
| 140 | Me | Me | OH | 2-CH2SMe | 1,2,3-triazol-1-yl |
| 141 | Me | Me | OH | 2-Cl | 1,2,3-triazol-1-yl |
| 142 | Me | Me | OH | 2-Me | 1,2,3-triazol-1-yl |
| 143 | Me | Me | OH | 2-SMe | 1,2,3-triazol-1-yl |
| 144 | Me | Me | OH | 2-SMe-3-Br | 1,2,3-triazol-1-yl |
| 145 | Me | Me | OH | 2-SMe-3-F | 1,2,3-triazol-1-yl |
| 146 | Me | Me | OH | 2-SMe-3-SMe | 1,2,3-triazol-1-yl |
| 147 | Me | Me | OH | 2-CF3 | 1,2,3-triazol-2-yl |
| 148 | Me | Me | OH | 2-CH2SMe | 1,2,3-triazol-2-yl |
| 149 | Me | Me | OH | 2-Cl | 1,2,3-triazol-2-yl |
| 150 | Me | Me | OH | 2-Me | 1,2,3-triazol-2-yl |
| 151 | Me | Me | OH | 2-SMe | 1,2,3-triazol-2-yl |
| 152 | Me | Me | OH | 2-SMe-3-Br | 1,2,3-triazol-2-yl |
| 153 | Me | Me | OH | 2-SMe-3-F | 1,2,3-triazol-2-yl |
| 154 | Me | Me | OH | 2-SMe-3-SMe | 1,2,3-triazol-2-yl |
| 155 | Me | Me | OH | 2-Br | 1,2,4-triazol-1-yl |
| 156 | Me | Me | OH | 2-CH2[(2-MeS)Ph] | 1,2,4-triazol-1-yl |
| 157 | Me | Me | OH | 2-CH2[(2-MeSO)Ph] | 1,2,4-triazol-1-yl |
| 158 | Me | Me | OH | 2-CH2[(2-MeSO2)Ph] | 1,2,4-triazol-1-yl |
| 159 | Me | Me | OH | 2-CH2N(Me)CO2Me | 1,2,4-triazol-1-yl |
| 160 | Me | Me | OH | 2-CH2N(Me)SO2Me | 1,2,4-triazol-1-yl |
| 161 | Me | Me | OH | 2-CH2Ph | 1,2,4-triazol-1-yl |
| 162 | Me | Me | OH | 2-CH2SMe | 1,2,4-triazol-1-yl |
| 163 | Me | Me | OH | 2-CH2SMe | 1,2,4-triazol-1-yl |
| 164 | Me | Me | OH | 2-CH2SO2Me | 1,2,4-triazol-1-yl |
| 165 | Me | Me | OH | 2-CH2SOMe | 1,2,4-triazol-1-yl |
| 166 | Me | Me | OH | 2-Cl | 1,2,4-triazol-1-yl |
| 167 | Me | Me | OH | 2-Me | 1,2,4-triazol-1-yl |
| 168 | Me | Me | OH | 2-Me-3-SMe | 1,2,4-triazol-1-yl |
| 169 | Me | Me | OH | 2-Me-3-SO2Me | 1,2,4-triazol-1-yl |
| 170 | Me | Me | OH | 2-Me-3-SOMe | 1,2,4-triazol-1-yl |
| 171 | Me | Me | OH | 2-NMeCO2Me | 1,2,4-triazol-1-yl |
| 172 | Me | Me | OH | 2-NMeSO2Me | 1,2,4-triazol-1-yl |
| 173 | Me | Me | OH | 2-OMe | 1,2,4-triazol-1-yl |
| 174 | Me | Me | OH | 2-OMe-3-SMe | 1,2,4-triazol-1-yl |
| 175 | Me | Me | OH | 2-OMe-3-SO2Me | 1,2,4-triazol-1-yl |
| 176 | Me | Me | OH | 2-OMe-3-SOMe | 1,2,4-triazol-1-yl |
| 177 | Me | Me | OH | 2-SMe | 1,2,4-triazol-1-yl |
| 178 | Me | Me | OH | 2-SMe-3-Br | 1,2,4-triazol-1-yl |
| 179 | Me | Me | OH | 2-SMe-3-Cl | 1,2,4-triazol-1-yl |
| 180 | Me | Me | OH | 2-SMe-3-F | 1,2,4-triazol-1-yl |
| 181 | Me | Me | OH | 2-SMe-3-OMe | 1,2,4-triazol-1-yl |
| 182 | Me | Me | OH | 2-SMe-3-SMe | 1,2,4-triazol-1-yl |
| 183 | Me | Me | OH | 2-SO2Me | 1,2,4-triazol-1-yl |
| 184 | Me | Me | OH | 2-SO2Me-3-Cl | 1,2,4-triazol-1-yl |
| 185 | Me | Me | OH | 2-SO2Me-3-OMe | 1,2,4-triazol-1-yl |
| 186 | Me | Me | OH | 2-SOMe | 1,2,4-triazol-1-yl |
| 187 | Me | Me | OH | 2-SOMe-3-Cl | 1,2,4-triazol-1-yl |
| 188 | Me | Me | OH | 2-SOMe-3-OMe | 1,2,4-triazol-1-yl |
| 189 | Me | Me | OH | 2-NO2 | 1,2,4-triazol-1-yl |
| 190 | Me | Me | OH | 2-CF3 | imidazol-1-yl |
| 191 | Me | Me | OH | 2-CH2SMe | imidazol-1-yl |
| 192 | Me | Me | OH | 2-Cl | imidazol-1-yl |
| 193 | Me | Me | OH | 2-Me | imidazol-1-yl |
| 194 | Me | Me | OH | 2-SMe | imidazol-1-yl |
| 195 | Me | Me | OH | 2-SMe-3-Br | imidazol-1-yl |
| 196 | Me | Me | OH | 2-SMe-3-F | imidazol-1-yl |
| 197 | Me | Me | OH | 2-SMe-3-SMe | imidazol-1-yl |
| 198 | Me | Me | OH | 2-CF3 | pyrazol-1-yl |
| 199 | Me | Me | OH | 2-CH2SMe | pyrazol-1-yl |
| 200 | Me | Me | OH | 2-Cl | pyrazol-1-yl |
| 201 | Me | Me | OH | 2-Me | pyrazol-1-yl |
| 202 | Me | Me | OH | 2-SMe | pyrazol-1-yl |
| 203 | Me | Me | OH | 2-CF3 | tetrazol-1-yl |
| 204 | Me | Me | OH | 2-SMe | tetrazol-1-yl |
| 205 | Me | Me | OH | 2-SMe-3-SMe | tetrazol-1-yl |
| 206 | H | H | OH | 2-CF3 | 3-Me-1,2,4-triazol-1-yl |
| 207 | H | Me | OH | 2-CF3 | 3-Me-1,2,4-triazol-1-yl |
| 208 | Me | Me | OH | 2-CF3 | 3-Me-1,2,4-triazol-1-yl |
| 563 | H | H | OH | 2-F | 1,2,4-triazol-1-yl |
| 564 | H | Me | OH | 2-F | 1,2,4-triazol-1-yl |
| 565 | Me | Me | OH | 2-F | 1,2,4-triazol-1-yl |

TABLE 2

| Cpd. No. | R6 | R7 | Q | (R2)n | (XR3)z |
|---|---|---|---|---|---|
| 209 | H | H | OH | 4-Br | 1,2,3-triazol-1-yl |
| 210 | H | H | OH | 4-CF3 | 1,2,3-triazol-1-yl |
| 211 | H | H | OH | 4-Cl | 1,2,3-triazol-1-yl |
| 212 | H | H | OH | 4-F | 1,2,3-triazol-1-yl |
| 213 | H | H | OH | 4-SMe | 1,2,3-triazol-1-yl |
| 214 | H | H | OH | 4-Br | 1,2,3-triazol-2-yl |
| 215 | H | H | OH | 4-CF3 | 1,2,3-triazol-2-yl |
| 216 | H | H | OH | 4-Cl | 1,2,3-triazol-2-yl |
| 217 | H | H | OH | 4-F | 1,2,3-triazol-2-yl |
| 218 | H | H | OH | 4-SMe | 1,2,3-triazol-2-yl |
| 219 | H | H | OH | 3,4-Cl2 | 1,2,4-triazol-1-yl |
| 220 | H | H | OH | 3,4-F2 | 1,2,4-triazol-1-yl |
| 221 | H | H | OH | 3-Br | 1,2,4-triazol-1-yl |
| 222 | H | H | OH | 3-CF3 | 1,2,4-triazol-1-yl |
| 223 | H | H | OH | 3-CH2SO2Me | 1,2,4-triazol-1-yl |
| 224 | H | H | OH | 3-CH2SO2Me | 1,2,4-triazol-1-yl |
| 225 | H | H | OH | 3-CH2SOMe | 1,2,4-triazol-1-yl |
| 226 | H | H | OH | 3-Cl | 1,2,4-triazol-1-yl |
| 227 | H | H | OH | 3-F | 1,2,4-triazol-1-yl |
| 228 | H | H | OH | 3-Me | 1,2,4-triazol-1-yl |
| 229 | H | H | OH | 3-Me-4-F | 1,2,4-triazol-1-yl |
| 230 | H | H | OH | 3-Me-4-SMe | 1,2,4-triazol-1-yl |
| 231 | H | H | OH | 3-OMe | 1,2,4-triazol-1-yl |
| 232 | H | H | OH | 3-SMe | 1,2,4-triazol-1-yl |
| 233 | H | H | OH | 3-SMe-4-F | 1,2,4-triazol-1-yl |
| 234 | H | H | OH | 3-SMe-4-OMe | 1,2,4-triazol-1-yl |
| 235 | H | H | OH | 3-SMe-4-SMe | 1,2,4-triazol-1-yl |
| 236 | H | H | OH | 3-SO2Me | 1,2,4-triazol-1-yl |
| 237 | H | H | OH | 3-SO2Me-4-F | 1,2,4-triazol-1-yl |
| 238 | H | H | OH | 3-SO2Me-4-OMe | 1,2,4-triazol-1-yl |
| 239 | H | H | OH | 3-SO2Me-4-SO2Me | 1,2,4-triazol-1-yl |
| 240 | H | H | OH | 3-SOMe | 1,2,4-triazol-1-yl |
| 241 | H | H | OH | 3-SOMe-4-F | 1,2,4-triazol-1-yl |
| 242 | H | H | OH | 3-SOMe-4-OMe | 1,2,4-triazol-1-yl |
| 243 | H | H | OH | 4-Br | 1,2,4-triazol-1-yl |
| 244 | H | H | OH | 4-CF3 | 1,2,4-triazol-1-yl |
| 245 | H | H | OH | 4-Cl | 1,2,4-triazol-1-yl |
| 246 | H | H | OH | 4-F | 1,2,4-triazol-1-yl |
| 247 | H | H | OH | 4-Me | 1,2,4-triazol-1-yl |
| 248 | H | H | OH | 4-OMe | 1,2,4-triazol-1-yl |
| 249 | H | H | OH | 4-SMe | 1,2,4-triazol-1-yl |
| 250 | H | H | OH | 4-SO2Me | 1,2,4-triazol-1-yl |
| 251 | H | H | OH | 4-SOMe | 1,2,4-triazol-1-yl |
| 252 | H | H | OH | — | 1,2,4-triazol-1-yl |
| 253 | H | H | OH | 4-Br | imidazol-1-yl |
| 254 | H | H | OH | 4-CF3 | imidazol-1-yl |
| 255 | H | H | OH | 4-Cl | imidazol-1-yl |
| 256 | H | H | OH | 4-F | imidazol-1-yl |
| 257 | H | H | OH | 4-SMe | imidazol-1-yl |
| 258 | H | H | OH | — | pyrazol-1-yl |
| 259 | H | H | OH | 4-Br | tetrazol-1-yl |
| 260 | H | H | OH | 4-CF3 | tetrazol-1-yl |
| 261 | H | H | OH | 4-Cl | tetrazol-1-yl |
| 262 | H | H | OH | 4-F | tetrazol-1-yl |

TABLE 2-continued

| Cpd. No. | R6 | R7 | Q | (R2)n | (XR3)z |
|---|---|---|---|---|---|
| 263 | H | H | OH | 4-SMe | tetrazol-1-yl |
| 264 | H | H | OH | 4-Br | benzimidazol-1-yl |
| 265 | H | H | OH | 4-CF3 | benzimidazol-1-yl |
| 266 | H | H | OH | 4-Cl | benzimidazol-1-yl |
| 267 | H | H | OH | 4-F | benzimidazol-1-yl |
| 268 | H | H | OH | 4-SMe | benzimidazol-1-yl |
| 269 | H | Me | OH | 4-Br | 1,2,3-triazol-1-yl |
| 270 | H | Me | OH | 4-CF3 | 1,2,3-triazol-1-yl |
| 271 | H | Me | OH | 4-Cl | 1,2,3-triazol-1-yl |
| 272 | H | Me | OH | 4-F | 1,2,3-triazol-1-yl |
| 273 | H | Me | OH | 4-SMe | 1,2,3-triazol-1-yl |
| 274 | H | Me | OH | 4-Br | 1,2,3-triazol-2-yl |
| 275 | H | Me | OH | 4-CF3 | 1,2,3-triazol-2-yl |
| 276 | H | Me | OH | 4-Cl | 1,2,3-triazol-2-yl |
| 277 | H | Me | OH | 4-F | 1,2,3-triazol-2-yl |
| 278 | H | Me | OH | 4-SMe | 1,2,3-triazol-2-yl |
| 279 | H | Me | OH | 3,4-Cl2 | 1,2,4-triazol-1-yl |
| 280 | H | Me | OH | 3,4-F2 | 1,2,4-triazol-1-yl |
| 281 | H | Me | OH | 3-Br | 1,2,4-triazol-1-yl |
| 282 | H | Me | OH | 3-CF3 | 1,2,4-triazol-1-yl |
| 283 | H | Me | OH | 3-CH2SO2Me | 1,2,4-triazol-1-yl |
| 284 | H | Me | OH | 3-CH2SO2Me | 1,2,4-triazol-1-yl |
| 285 | H | Me | OH | 3-CH2SOMe | 1,2,4-triazol-1-yl |
| 286 | H | Me | OH | 3-Cl | 1,2,4-triazol-1-yl |
| 287 | H | Me | OH | 3-F | 1,2,4-triazol-1-yl |
| 288 | H | Me | OH | 3-Me | 1,2,4-triazol-1-yl |
| 289 | H | Me | OH | 3-Me-4-F | 1,2,4-triazol-1-yl |
| 290 | H | Me | OH | 3-Me-4-SMe | 1,2,4-triazol-1-yl |
| 291 | H | Me | OH | 3-OMe | 1,2,4-triazol-1-yl |
| 292 | H | Me | OH | 3-SMe | 1,2,4-triazol-1-yl |
| 293 | H | Me | OH | 3-SMe-4-F | 1,2,4-triazol-1-yl |
| 294 | H | Me | OH | 3-SMe-4-OMe | 1,2,4-triazol-1-yl |
| 295 | H | Me | OH | 3-SMe-4-SMe | 1,2,4-triazol-1-yl |
| 296 | H | Me | OH | 3-SO2Me | 1,2,4-triazol-1-yl |
| 297 | H | Me | OH | 3-SO2Me-4-F | 1,2,4-triazol-1-yl |
| 298 | H | Me | OH | 3-SO2Me-4-OMe | 1,2,4-triazol-1-yl |
| 299 | H | Me | OH | 3-SO2Me-4-SO2Me | 1,2,4-triazol-1-yl |
| 300 | H | Me | OH | 3-SOMe | 1,2,4-triazol-1-yl |
| 301 | H | Me | OH | 3-SOMe-4-F | 1,2,4-triazol-1-yl |
| 302 | H | Me | OH | 3-SOMe-4-OMe | 1,2,4-triazol-1-yl |
| 303 | H | Me | OH | 4-Br | 1,2,4-triazol-1-yl |
| 304 | H | Me | OH | 4-CF3 | 1,2,4-triazol-1-yl |
| 305 | H | Me | OH | 4-Cl | 1,2,4-triazol-1-yl |
| 306 | H | Me | OH | 4-F | 1,2,4-triazol-1-yl |
| 307 | H | Me | OH | 4-Me | 1,2,4-triazol-1-yl |
| 308 | H | Me | OH | 4-OMe | 1,2,4-triazol-1-yl |
| 309 | H | Me | OH | 4-SMe | 1,2,4-triazol-1-yl |
| 310 | H | Me | OH | 4-SO2Me | 1,2,4-triazol-1-yl |
| 311 | H | Me | OH | 4-SOMe | 1,2,4-triazol-1-yl |
| 312 | H | Me | OH | — | 1,2,4-triazol-1-yl |
| 313 | H | Me | OH | 4-Br | imidazol-1-yl |
| 314 | H | Me | OH | 4-CF3 | imidazol-1-yl |
| 315 | H | Me | OH | 4-Cl | imidazol-1-yl |
| 316 | H | Me | OH | 4-F | imidazol-1-yl |
| 317 | H | Me | OH | 4-SMe | imidazol-1-yl |
| 318 | H | Me | OH | — | pyrazol-1-yl |
| 319 | H | Me | OH | 4-Br | tetrazol-1-yl |
| 320 | H | Me | OH | 4-CF3 | tetrazol-1-yl |
| 321 | H | Me | OH | 4-Cl | tetrazol-1-yl |
| 322 | H | Me | OH | 4-F | tetrazol-1-yl |
| 323 | H | Me | OH | 4-SMe | tetrazol-1-yl |
| 324 | H | Me | OH | 4-Br | benzimidazol-1-yl |
| 325 | H | Me | OH | 4-CF3 | benzimidazol-1-yl |
| 326 | H | Me | OH | 4-Cl | benzimidazol-1-yl |
| 327 | H | Me | OH | 4-F | benzimidazol-1-yl |
| 328 | H | Me | OH | 4-SMe | benzimidazol-1-yl |
| 329 | Me | Me | OH | 4-Br | 1,2,3-triazol-1-yl |
| 330 | Me | Me | OH | 4-CF3 | 1,2,3-triazol-1-yl |
| 331 | Me | Me | OH | 4-Cl | 1,2,3-triazol-1-yl |
| 332 | Me | Me | OH | 4-F | 1,2,3-triazol-1-yl |
| 333 | Me | Me | OH | 4-SMe | 1,2,3-triazol-1-yl |
| 334 | Me | Me | OH | 4-Br | 1,2,3-triazol-2-yl |
| 335 | Me | Me | OH | 4-CF3 | 1,2,3-triazol-2-yl |
| 336 | Me | Me | OH | 4-Cl | 1,2,3-triazol-2-yl |
| 337 | Me | Me | OH | 4-F | 1,2,3-triazol-2-yl |
| 338 | Me | Me | OH | 4-SMe | 1,2,3-triazol-2-yl |
| 339 | Me | Me | OH | 3,4-Cl2 | 1,2,4-triazol-1-yl |
| 340 | Me | Me | OH | 3,4-F2 | 1,2,4-triazol-1-yl |
| 341 | Me | Me | OH | 3-Br | 1,2,4-triazol-1-yl |
| 342 | Me | Me | OH | 3-CF3 | 1,2,4-triazol-1-yl |
| 343 | Me | Me | OH | 3-CH2SO2Me | 1,2,4-triazol-1-yl |
| 344 | Me | Me | OH | 3-CH2SO2Me | 1,2,4-triazol-1-yl |
| 345 | Me | Me | OH | 3-CH2SOMe | 1,2,4-triazol-1-yl |
| 346 | Me | Me | OH | 3-Cl | 1,2,4-triazol-1-yl |
| 347 | Me | Me | OH | 3-F | 1,2,4-triazol-1-yl |
| 348 | Me | Me | OH | 3-Me | 1,2,4-triazol-1-yl |
| 349 | Me | Me | OH | 3-Me-4-F | 1,2,4-triazol-1-yl |
| 350 | Me | Me | OH | 3-Me-4-SMe | 1,2,4-triazol-1-yl |
| 351 | Me | Me | OH | 3-OMe | 1,2,4-triazol-1-yl |
| 352 | Me | Me | OH | 3-SMe | 1,2,4-triazol-1-yl |
| 353 | Me | Me | OH | 3-SMe-4-F | 1,2,4-triazol-1-yl |
| 354 | Me | Me | OH | 3-SMe-4-OMe | 1,2,4-triazol-1-yl |
| 355 | Me | Me | OH | 3-SMe-4-SMe | 1,2,4-triazol-1-yl |
| 356 | Me | Me | OH | 3-SO2Me | 1,2,4-triazol-1-yl |
| 357 | Me | Me | OH | 3-SO2Me-4-F | 1,2,4-triazol-1-yl |
| 358 | Me | Me | OH | 3-SO2Me-4-OMe | 1,2,4-triazol-1-yl |
| 359 | Me | Me | OH | 3-SO2Me-4-SO2Me | 1,2,4-triazol-1-yl |
| 360 | Me | Me | OH | 3-SOMe | 1,2,4-triazol-1-yl |
| 361 | Me | Me | OH | 3-SOMe-4-F | 1,2,4-triazol-1-yl |
| 362 | Me | Me | OH | 3-SOMe-4-OMe | 1,2,4-triazol-1-yl |
| 363 | Me | Me | OH | 4-Br | 1,2,4-triazol-1-yl |
| 364 | Me | Me | OH | 4-CF3 | 1,2,4-triazol-1-yl |
| 365 | Me | Me | OH | 4-Cl | 1,2,4-triazol-1-yl |
| 366 | Me | Me | OH | 4-F | 1,2,4-triazol-1-yl |
| 367 | Me | Me | OH | 4-Me | 1,2,4-triazol-1-yl |
| 368 | Me | Me | OH | 4-OMe | 1,2,4-triazol-1-yl |
| 369 | Me | Me | OH | 4-SMe | 1,2,4-triazol-1-yl |
| 370 | Me | Me | OH | 4-SO2Me | 1,2,4-triazol-1-yl |
| 371 | Me | Me | OH | 4-SOMe | 1,2,4-triazol-1-yl |
| 372 | Me | Me | OH | — | 1,2,4-triazol-1-yl |
| 373 | Me | Me | OH | 4-Br | imidazol-1-yl |
| 374 | Me | Me | OH | 4-CF3 | imidazol-1-yl |
| 375 | Me | Me | OH | 4-Cl | imidazol-1-yl |
| 376 | Me | Me | OH | 4-F | imidazol-1-yl |
| 377 | Me | Me | OH | 4-SMe | imidazol-1-yl |
| 378 | Me | Me | OH | — | pyrazol-1-yl |
| 379 | Me | Me | OH | 4-Br | tetrazol-1-yl |
| 380 | Me | Me | OH | 4-CF3 | tetrazol-1-yl |
| 381 | Me | Me | OH | 4-Cl | tetrazol-1-yl |
| 382 | Me | Me | OH | 4-F | tetrazol-1-yl |
| 383 | Me | Me | OH | 4-SMe | tetrazol-1-yl |
| 384 | Me | Me | OH | 4-Br | benzimidazol-1-yl |
| 385 | Me | Me | OH | 4-CF3 | benzimidazol-1-yl |
| 386 | Me | Me | OH | 4-Cl | benzimidazol-1-yl |
| 387 | Me | Me | OH | 4-F | benzimidazol-1-yl |
| 388 | Me | Me | OH | 4-SMe | benzimidazol-1-yl |
| 389 | H | H | OH | 4-Br | CH2-(triazol-1-yl) |
| 390 | H | H | OH | 4-Cl | CH2-(triazol-1-yl) |
| 391 | H | H | OH | 4-F | CH2-(triazol-1-yl) |
| 392 | H | H | OH | 4-CF3 | CH2-(triazol-1-yl) |
| 393 | H | H | OH | 4-OF3 | CH2-(triazol-1-yl) |
| 394 | H | H | OH | 4-Me | CH2-(triazol-1-yl) |

TABLE 3

| Cpd. No. | R6 | R7 | Q | (R2)n | R3 |
|---|---|---|---|---|---|
| 395 | H | H | OH | 2-Br | 1,2,3-triazol-1-yl |
| 396 | H | H | OH | 2-CF3 | 1,2,3-triazol-1-yl |
| 397 | H | H | OH | 2-CH2SMe | 1,2,3-triazol-1-yl |
| 398 | H | H | OH | 2-Cl | 1,2,3-triazol-1-yl |
| 399 | H | H | OH | 2-F | 1,2,3-triazol-1-yl |
| 400 | H | H | OH | 2-SMe | 1,2,3-triazol-1-yl |
| 401 | H | H | OH | 2-SMe-4-Br | 1,2,3-triazol-1-yl |
| 402 | H | H | OH | 2-SMe-4-CF3 | 1,2,3-triazol-1-yl |
| 403 | H | H | OH | 2-SMe-4-Cl | 1,2,3-triazol-1-yl |
| 404 | H | H | OH | 2-SMe-4-F | 1,2,3-triazol-1-yl |
| 405 | H | H | OH | 2-SMe-4-SMe | 1,2,3-triazol-1-yl |

TABLE 3-continued

| Cpd. No. | R6 | R7 | Q | (R2)n | R3 |
|---|---|---|---|---|---|
| 406 | H | H | OH | 2-SO2Me | 1,2,3-triazol-1-yl |
| 407 | H | H | OH | 2-SO2Me-4-SO2Me | 1,2,3-triazol-1-yl |
| 408 | H | H | OH | 2-SOMe | 1,2,3-triazol-1-yl |
| 409 | H | H | OH | 2-Br | 1,2,4-triazol-1-yl |
| 410 | H | H | OH | 2-CF3 | 1,2,4-triazol-1-yl |
| 411 | H | H | OH | 2-CH2SMe | 1,2,4-triazol-1-yl |
| 412 | H | H | OH | 2-Cl | 1,2,4-triazol-1-yl |
| 413 | H | H | OH | 2-F | 1,2,4-triazol-1-yl |
| 414 | H | H | OH | 2-SMe | 1,2,4-triazol-1-yl |
| 415 | H | H | OH | 2-SMe-4-Br | 1,2,4-triazol-1-yl |
| 416 | H | H | OH | 2-SMe-4-CF3 | 1,2,4-triazol-1-yl |
| 417 | H | H | OH | 2-SMe-4-Cl | 1,2,4-triazol-1-yl |
| 418 | H | H | OH | 2-SMe-4-F | 1,2,4-triazol-1-yl |
| 419 | H | H | OH | 2-SMe-4-SMe | 1,2,4-triazol-1-yl |
| 420 | H | H | OH | 2-SO2Me | 1,2,4-triazol-1-yl |
| 421 | H | H | OH | 2-SO2Me-4-SO2Me | 1,2,4-triazol-1-yl |
| 422 | H | H | OH | 2-SOMe | 1,2,4-triazol-1-yl |
| 423 | H | H | OH | 2-Br | imidazol-1-yl |
| 424 | H | H | OH | 2-CF3 | imidazol-1-yl |
| 425 | H | H | OH | 2-CH2SMe | imidazol-1-yl |
| 426 | H | H | OH | 2-Cl | imidazol-1-yl |
| 427 | H | H | OH | 2-F | imidazol-1-yl |
| 428 | H | H | OH | 2-SMe | imidazol-1-yl |
| 429 | H | H | OH | 2-SMe-4-Br | imidazol-1-yl |
| 430 | H | H | OH | 2-SMe-4-CF3 | imidazol-1-yl |
| 431 | H | H | OH | 2-SMe-4-Cl | imidazol-1-yl |
| 432 | H | H | OH | 2-SMe-4-F | imidazol-1-yl |
| 433 | H | H | OH | 2-SMe-4-SMe | imidazol-1-yl |
| 434 | H | H | OH | 2-SO2Me | imidazol-1-yl |
| 435 | H | H | OH | 2-SO2Me-4-SO2Me | imidazol-1-yl |
| 436 | H | H | OH | 2-SOMe | imidazol-1-yl |
| 437 | H | H | OH | 2-Br | tetrazol-1-yl |
| 438 | H | H | OH | 2-CF3 | tetrazol-1-yl |
| 439 | H | H | OH | 2-CH2SMe | tetrazol-1-yl |
| 440 | H | H | OH | 2-Cl | tetrazol-1-yl |
| 441 | H | H | OH | 2-F | tetrazol-1-yl |
| 442 | H | H | OH | 2-SMe | tetrazol-1-yl |
| 443 | H | H | OH | 2-SMe-4-Br | tetrazol-1-yl |
| 444 | H | H | OH | 2-SMe-4-CF3 | tetrazol-1-yl |
| 445 | H | H | OH | 2-SMe-4-Cl | tetrazol-1-yl |
| 446 | H | H | OH | 2-SMe-4-F | tetrazol-1-yl |
| 447 | H | H | OH | 2-SMe-4-SMe | tetrazol-1-yl |
| 448 | H | H | OH | 2-SO2Me | tetrazol-1-yl |
| 449 | H | H | OH | 2-SO2Me-4-SO2Me | tetrazol-1-yl |
| 450 | H | H | OH | 2-SOMe | tetrazol-1-yl |
| 451 | H | Me | OH | 2-Br | 1,2,3-triazol-1-yl |
| 452 | H | Me | OH | 2-CF3 | 1,2,3-triazol-1-yl |
| 453 | H | Me | OH | 2-CH2SMe | 1,2,3-triazol-1-yl |
| 454 | H | Me | OH | 2-Cl | 1,2,3-triazol-1-yl |
| 455 | H | Me | OH | 2-F | 1,2,3-triazol-1-yl |
| 456 | H | Me | OH | 2-SMe | 1,2,3-triazol-1-yl |
| 457 | H | Me | OH | 2-SMe-4-Br | 1,2,3-triazol-1-yl |
| 458 | H | Me | OH | 2-SMe-4-CF3 | 1,2,3-triazol-1-yl |
| 459 | H | Me | OH | 2-SMe-4-Cl | 1,2,3-triazol-1-yl |
| 460 | H | Me | OH | 2-SMe-4-F | 1,2,3-triazol-1-yl |
| 461 | H | Me | OH | 2-SMe-4-SMe | 1,2,3-triazol-1-yl |
| 462 | H | Me | OH | 2-SO2Me | 1,2,3-triazol-1-yl |
| 463 | H | Me | OH | 2-SO2Me-4-SO2Me | 1,2,3-triazol-1-yl |
| 464 | H | Me | OH | 2-SOMe | 1,2,3-triazol-1-yl |
| 465 | H | Me | OH | 2-Br | 1,2,4-triazol-1-yl |
| 466 | H | Me | OH | 2-CF3 | 1,2,4-triazol-1-yl |
| 467 | H | Me | OH | 2-CH2SMe | 1,2,4-triazol-1-yl |
| 468 | H | Me | OH | 2-Cl | 1,2,4-triazol-1-yl |
| 469 | H | Me | OH | 2-F | 1,2,4-triazol-1-yl |
| 470 | H | Me | OH | 2-SMe | 1,2,4-triazol-1-yl |
| 471 | H | Me | OH | 2-SMe-4-Br | 1,2,4-triazol-1-yl |
| 472 | H | Me | OH | 2-SMe-4-CF3 | 1,2,4-triazol-1-yl |
| 473 | H | Me | OH | 2-SMe-4-Cl | 1,2,4-triazol-1-yl |
| 474 | H | Me | OH | 2-SMe-4-F | 1,2,4-triazol-1-yl |
| 475 | H | Me | OH | 2-SMe-4-SMe | 1,2,4-triazol-1-yl |
| 476 | H | Me | OH | 2-SO2Me | 1,2,4-triazol-1-yl |
| 477 | H | Me | OH | 2-SO2Me-4-SO2Me | 1,2,4-triazol-1-yl |
| 478 | H | Me | OH | 2-SOMe | 1,2,4-triazol-1-yl |
| 479 | H | Me | OH | 2-Br | imidazol-1-yl |
| 480 | H | Me | OH | 2-CF3 | imidazol-1-yl |
| 481 | H | Me | OH | 2-CH2SMe | imidazol-1-yl |
| 482 | H | Me | OH | 2-Cl | imidazol-1-yl |
| 483 | H | Me | OH | 2-F | imidazol-1-yl |
| 484 | H | Me | OH | 2-SMe | imidazol-1-yl |
| 485 | H | Me | OH | 2-SMe-4-Br | imidazol-1-yl |
| 486 | H | Me | OH | 2-SMe-4-CF3 | imidazol-1-yl |
| 487 | H | Me | OH | 2-SMe-4-Cl | imidazol-1-yl |
| 488 | H | Me | OH | 2-SMe-4-F | imidazol-1-yl |
| 489 | H | Me | OH | 2-SMe-4-SMe | imidazol-1-yl |
| 490 | H | Me | OH | 2-SO2Me | imidazol-1-yl |
| 491 | H | Me | OH | 2-SO2Me-4-SO2Me | imidazol-1-yl |
| 492 | H | Me | OH | 2-SOMe | imidazol-1-yl |
| 493 | H | Me | OH | 2-Br | tetrazol-1-yl |
| 494 | H | Me | OH | 2-CF3 | tetrazol-1-yl |
| 495 | H | Me | OH | 2-CH2SMe | tetrazol-1-yl |
| 496 | H | Me | OH | 2-Cl | tetrazol-1-yl |
| 497 | H | Me | OH | 2-F | tetrazol-1-yl |
| 498 | H | Me | OH | 2-SMe | tetrazol-1-yl |
| 499 | H | Me | OH | 2-SMe-4-Br | tetrazol-1-yl |
| 500 | H | Me | OH | 2-SMe-4-CF3 | tetrazol-1-yl |
| 501 | H | Me | OH | 2-SMe-4-Cl | tetrazol-1-yl |
| 502 | H | Me | OH | 2-SMe-4-F | tetrazol-1-yl |
| 503 | H | Me | OH | 2-SMe-4-SMe | tetrazol-1-yl |
| 504 | H | Me | OH | 2-SO2Me | tetrazol-1-yl |
| 505 | H | Me | OH | 2-SO2Me-4-SO2Me | tetrazol-1-yl |
| 506 | H | Me | OH | 2-SOMe | tetrazol-1-yl |
| 507 | Me | Me | OH | 2-Br | 1,2,3-triazol-1-yl |
| 508 | Me | Me | OH | 2CF3 | 1,2,3-triazol-1-yl |
| 509 | Me | Me | OH | 2-CH2SMe | 1,2,3-triazol-1-yl |
| 510 | Me | Me | OH | 2-Cl | 1,2,3-triazol-1-yl |
| 511 | Me | Me | OH | 2-F | 1,2,3-triazol-1-yl |
| 512 | Me | Me | OH | 2-SMe | 1,2,3-triazol-1-yl |
| 513 | Me | Me | OH | 2-SMe-4-Br | 1,2,3-triazol-1-yl |
| 514 | Me | Me | OH | 2-SMe-4-CF3 | 1,2,3-triazol-1-yl |
| 515 | Me | Me | OH | 2-SMe-4-Cl | 1,2,3-triazol-1-yl |
| 516 | Me | Me | OH | 2-SMe-4-F | 1,2,3-triazol-1-yl |
| 517 | Me | Me | OH | 2-SMe-4-SMe | 1,2,3-triazol-1-yl |
| 518 | Me | Me | OH | 2-SO2Me | 1,2,3-triazol-1-yl |
| 519 | Me | Me | OH | 2-SO2Me-4-SO2Me | 1,2,3-triazol-1-yl |
| 520 | Me | Me | OH | 2-SOMe | 1,2,3-triazol-1-yl |
| 521 | Me | Me | OH | 2-Br | 1,2,4-triazol-1-yl |
| 522 | Me | Me | OH | 2-CF3 | 1,2,4-triazol-1-yl |
| 523 | Me | Me | OH | 2-CH2SMe | 1,2,4-triazol-1-yl |
| 524 | Me | Me | OH | 2-Cl | 1,2,4-triazol-1-yl |
| 525 | Me | Me | OH | 2-F | 1,2,4-triazol-1-yl |
| 526 | Me | Me | OH | 2-SMe | 1,2,4-triazol-1-yl |
| 527 | Me | Me | OH | 2-SMe-4-Br | 1,2,4-triazol-1-yl |
| 528 | Me | Me | OH | 2-SMe-4-CF3 | 1,2,4-triazol-1-yl |
| 529 | Me | Me | OH | 2-SMe-4-Cl | 1,2,4-triazol-1-yl |
| 530 | Me | Me | OH | 2-SMe-4-F | 1,2,4-triazol-1-yl |
| 531 | Me | Me | OH | 2-SMe-4-SMe | 1,2,4-triazol-1-yl |
| 532 | Me | Me | OH | 2-SO2Me | 1,2,4-triazol-1-yl |
| 533 | Me | Me | OH | 2-SO2Me-4-SO2Me | 1,2,4-triazol-1-yl |
| 534 | Me | Me | OH | 2-SOMe | 1,2,4-triazol-1-yl |
| 535 | Me | Me | OH | 2-Br | imidazol-1-yl |
| 536 | Me | Me | OH | 2-CF3 | imidazol-1-yl |
| 537 | Me | Me | OH | 2-CH2SMe | imidazol-1-yl |
| 538 | Me | Me | OH | 2-Cl | imidazol-1-yl |
| 539 | Me | Me | OH | 2-F | imidazol-1-yl |
| 540 | Me | Me | OH | 2-SMe | imidazol-1-yl |
| 541 | Me | Me | OH | 2-SMe-4-Br | imidazol-1-yl |
| 542 | Me | Me | OH | 2-SMe-4-CF3 | imidazol-1-yl |
| 543 | Me | Me | OH | 2-SMe-4-Cl | imidazol-1-yl |
| 544 | Me | Me | OH | 2-SMe-4-F | imidazol-1-yl |
| 545 | Me | Me | OH | 2-SMe-4-SMe | imidazol-1-yl |
| 546 | Me | Me | OH | 2-SO2Me | imidazol-1-yl |
| 547 | Me | Me | OH | 2-SO2Me-4-SO2Me | imidazol-1-yl |
| 548 | Me | Me | OH | 2-SOMe | imidazol-1-yl |
| 549 | Me | Me | OH | 2-Br | tetrazol-1-yl |
| 550 | Me | Me | OH | 2-CF3 | tetrazol-1-yl |
| 551 | Me | Me | OH | 2-CH2SMe | tetrazol-1-yl |
| 552 | Me | Me | OH | 2-Cl | tetrazol-1-yl |
| 553 | Me | Me | OH | 2-F | tetrazol-1-yl |
| 554 | Me | Me | OH | 2-SMe | tetrazol-1-yl |
| 555 | Me | Me | OH | 2-SMe-4-Br | tetrazol-1-yl |
| 556 | Me | Me | OH | 2-SMe-4-CF3 | tetrazol-1-yl |
| 557 | Me | Me | OH | 2-SMe-4-Cl | tetrazol-1-yl |

TABLE 3-continued

| Cpd. No. | R6 | R7 | Q | (R2)n | R3 |
|---|---|---|---|---|---|
| 558 | Me | Me | OH | 2-SMe-4-F | tetrazol-1-yl |
| 559 | Me | Me | OH | 2-SMe-4-SMe | tetrazol-1-yl |
| 560 | Me | Me | OH | 2-SO2Me | tetrazol-1-yl |
| 561 | Me | Me | OH | 2-SO2Me-4-SO2Me | tetrazol-1-yl |
| 562 | Me | Me | OH | 2-SOMe | tetrazol-1-yl |

Compounds of formula (I) may be prepared by the application or adaptation of known methods (i.e. methods heretofore used or described in the literature), for example as hereinafter described.

In the following description where symbols appearing in formulae are not specifically defined, it is to be understood that they are "as hereinbefore defined" in accordance with the first definition of each symbol in the specification.

It is to be understood that in the descriptions of the following processes the sequences may be performed in different orders, and that suitable protecting groups may be required to achieve the compounds sought.

According to a feature of the present invention compounds of formula (I) wherein the various symbols are as defined above and Q represents hydroxy may be prepared by the rearrangement of a compound of formula (VII), (VIII), (IX) or (X):

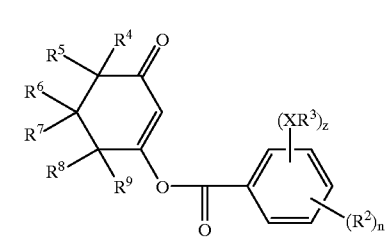
(VII)

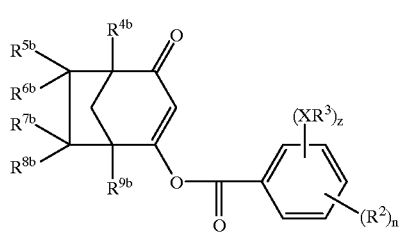
(VIII)

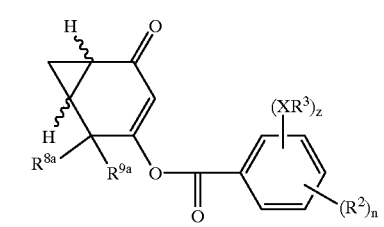
(IX)

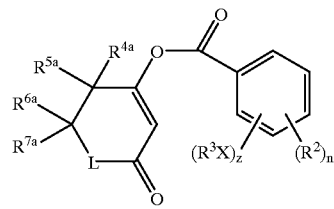
(X)

wherein the various symbols are as defined above, by reaction with a source of cyanide in the presence of a base. Cyanide sources include metal cyanides for example alkali metal cyanides such as sodium cyanide, hydrogen cyanide, or cyanhydrins of dialkyl ketones preferably acetone cyanhydrin. Generally up to 0.5 equivalent (preferably 0.1 equivalent) of cyanide source is employed. Suitable bases include trialkylamines such as triethylamine, or pyridine or alkali metal carbonates such as potassium carbonate. Generally 14 equivalents (preferably 2 equivalents) of the base is used. Solvents which may be used include toluene, acetonitrile, dichloromethane or preferably 1,2-dichloroethane. The reaction is generally performed at a temperature of from 0° C.–60° C. (generally at 20° C.–30° C.).

The above ester intermediates of formula (VII), (VIII), (IX) or (X) may be prepared by the reaction of the corresponding cyclohexane-1,3-dione derivatives of formula (XI), (XII), (XIII) or (XXIV) (which are represented here as the enol tautomer forms):

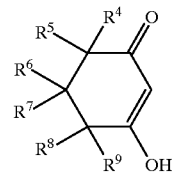
(XI)

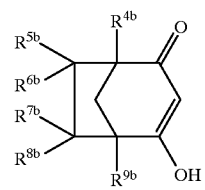
(XII)

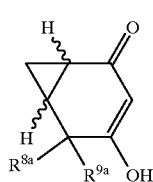
(XIII)

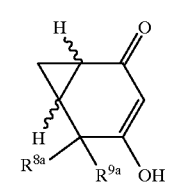
(XIV)

wherein the various symbols are as defined above, with an acid chloride of formula (XV):

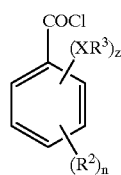

(XV)

wherein R², R³, X, z and n are as defined above. The reaction is generally performed in the presence of a base preferably a trialkylamine such as triethylamine, or an alkali metal carbonate such as potassium carbonate, in a solvent such as dichloromethane, dichloroethane, acetonitrile, N,N-dimethylformamide or tetrahydrofuran. One to 1.1 equivalents of the base is generally employed and the reaction is generally conducted at a temperature of from about −20° C. to about 50° C. (preferably 0° C. to 30° C.). Compounds of formula (VII), (VIII), (IX) and (X) are novel and as such constitute a further feature of the invention.

Optionally the reaction to form a compound of formula (I) by the reaction of a compound of formula (XV) with a compound of formula (XI), (XII), (XIII) or (XIV) to give ester intermediates of formula (VII), (VIII), (IX) or (X), and the subsequent reaction with a source of cyanide may be performed in one pot. In such cases the intermediate esters are not isolated but are treated in situ with the additional base and cyanide source required for the rearrangement process to occur, and according to the above process description.

It is understood that when unsymmetrical diones of formulae (XI), (XII), (XIII) and (XIV) are employed in the above reaction, that the isomeric esters in which the position of the ring carbonyl and ester groups is reversed may be formed, and that the process is applicable for the formation of all such isomeric forms.

According to a further feature of the present invention compounds of formula (I) wherein the various symbols are as defined above and Q represents SR²¹ or SR²² may be prepared by reaction of the corresponding compound of formula (I) wherein Q represents hydroxy with a chlorinating agent, generally oxalyl chloride, in an inert solvent such as dichloromethane and preferably in the presence of a catalyst such as N,N-dimethylformamide and at a temperature of from −20° C. to 50° C. (preferably from 0° C. to 30° C.) to give the intermediate chloride of formula (I) wherein Q is replaced by a chlorine atom. These intermediates are not generally isolated and are reacted in situ with a thiophenol of formula (XVI) or thiol of formula (XVII):

R²¹SH    (XVI)

R²²SH    (XVII)

wherein R²¹ and R²² are as defined above, in the presence of a base such as a trialkylamine, for example triethylamine, in an inert solvent such as dichloromethane or tetrahydrofuran, and at a temperature of from −20° C. to 50° C. (preferably from 0° C. to 30° C.).

According to a further feature of the present invention compounds in which p or q is one or two may be prepared by the oxidation of the sulphur atom of the corresponding compounds in which p or q is 0 or 1. The oxidation of the sulphur atom is generally carried out using for example 3-chloroperoxybenzoic acid in an inert solvent such as dichloromethane at a temperature from −40° C. to room temperature.

Compounds of formula (XV) may be prepared by the reaction of the corresponding benzoic acid derivative of formula (XVIII):

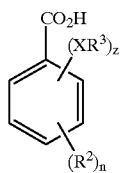

(XVIII)

with a chlorinating agent such as thionyl chloride or oxalyl chloride according to known procedures. Certain benzoic acids of formula (XVIII) are novel and as such constitute a further feature of the invention.

Compounds of formula (XI), (XII), (XIII) and (XIV) are known or may be prepared by known methods.

The following non-limiting Examples illustrate the preparation of compounds of formula (I) and the Reference Examples illustrate the preparation of intermediates in their synthesis. NMR Spectra are recorded as d (ppm) in deuterochloroform as solvent (unless otherwise stated).

EXAMPLE 1

To a solution of 3-[4-(1,2,4-triazol-1-yl)-2-trifluoromethylbenzoyloxy]cyclohex-2-en-1-one (2.90 g) in acetonitrile was added triethylamine (1.67 g) and acetone cyanohydrin (0.3 ml) at 20° C. The mixture was stirred for 3 days, evaporated and the residue diluted (ethyl acetate and aqueous citric acid). The organic layer was dried (magnesium sulfate), evaporated and the residue purified by chromatography eluting with ethyl acetate/hexane to give 2-[4-(1,2,4-triazol- 1-yl)-2-trifluoromethylbenzoyl]cyclohexane-1,3-dione as a colourless solid (Compound 1, 1.75 g), NMR 2.06(m,2H), 2.42(t,2H), 2.82(t,1H), 7.36(d, 1H), 7.90(m,1H), 8.05(s,1H), 8.15(s,1H), 8.65(s,1H).

By proceeding in a similar manner the following compounds were also prepared:

5,5-dimethyl-2-[4-(1,2,4-triazol-1-yl)-2-trifluoromethylbenzoyl]cyclohexane-1,3-dione (Compound 3), NMR 1.24(6H,s), 2.29(2H,s), 2.68(2H,s), 7.34(1 H,d), 7.89(1 H,d), 8.05(1H,s), 8.14(1 H,s), 8.66(1 H,s); 5-methyl-2-[4-(1,2,4-triazol-1-yl)-2-trifluoromethylbenzoyl]cyclohexane-1,3-dione (Compound 88), NMR 1.12 (d, 1H), 1.70 (s, 1H), 2.11–2.46 (m, 3H), 2.67–2.80 (m, 2H), 7.36 (d, 1H9, 7.92 (d, 1H), 8.08 (s, 1H), 8.16 (s, 1H), 8.73 (s, 1H);

2-[2-chloro-4-(1,2,4-triazol-1-yl)benzoyl]cyclohexane-1,3-dione (Compound 31), NMR 2.08 (m, 2H), 2.48 (m, 2H), 2.81 (m, 2H), 7.36 (d, 1H), 7.67 (d, 1H), 7.79 (s, 1H), 8.12 (s, 1H), 8.60 (s, 1H);

5,5-dimethyl-2-[2-chloro-4-(1,2,4-triazol-1-yl)benzoyl]cyclohexane-1,3-dione (Compound 166), NMR 1.43 (s, 6H), 2.35 (s, 2H), 2.68 (s, 2H), 7.37 (d, 1H), 7.67 (d, 1H), 7.78 (s, 1H), 8.12 (s, 1H), 8.61 (s, 1H);

5-methyl-2-[2-chloro-4-(1,2,4-triazol-1-yl)benzoyl]cyclohexane-1,3-dione (Compound 99), NMR 1.14 (d, 3H), 1.65 (s, 1H), 2.26–2.40 (m, 1H), 2.47–2.60 (m, 2H), 2.78–2.92 (m, 2H), 7.36 (d, 1H), 7.67 (d, 1H), 7.78 (s, 1H), 8.12 (s, 1H), 8.60 (s, 1H);

2-[2-methylthio-4-(1,2,4-triazol-1-yl)benzoyl]cyclohexane-1,3-dione (Compound 42), NMR 2.0(m,2H), 2.3(m,2H), 2.4(s,2H), 2.7(m,2H), 7.2(d,1H), 7.4(d,1H), 7.6 (s,1H), 8.0(s,1H), 8.6(s,1H); and 2-[2-methyl-4-(1,2,4-triazol-1-yl)benzoyl]cyclohexane-1,3-dione (Compound 32), NMR 2.0(m,2H), 2.3(s,2H), 2.4(m,2H), 2.8(m,2H), 7.2(d,1H), 7.5(d,1H), 7.6(s,1H), 8.1(s,1H), 8.6(s,1H).

EXAMPLE 2

To a solution of 2-[4-(1,2,4-triazol-1-yl)-2-trifluoromethylbenzoyl]cyclohexane-1,3-dione (1.42 g) in dry dichloromethane was added a catalytic amount of N,N-dimethylformamide followed by oxalyl chloride (0.9 ml) dropwise at 20° C. The mixture was stirred until a clear solution was obtained and then evaporated. To a suspension of the residue in dry tetrahydrofuran was added thiophenol (0.51 g) and triethylamine (0.93 g) dropwise at 0° C. The mixture was stirred at 20° C. for one day, then aqueous citric acid and ethyl acetate added. The organic layer was dried (magnesium sulfate), evaporated and the residue purified by chromatography eluting with ethyl acetate/hexane to give 3-phenylthio-2-[4-(1,2,4-triazol-1-yl)-2-trifluoromethylbenzoyl]cyclohex-2-ene-1-one (Compound 2, 0.93 g) as a yellow solid, NMR 1.92(m,2H), 2.36(t,2H), 2.48(t,2H), 7.40–7.62(m,6H), 7.92(dd,1H), 8.04(d,1H),8.15 (s,1H),8.66(s,1H).

Reference Example 1

To a suspension of 4-(1,2,4-triazol-1-yl)-2-trifluoromethylbenzoic acid (3.32 g) and a catalytic amount of N,N-dimethylformamide in dichloromethane was added oxalyl chloride (2.5 ml) dropwise at 20° C. The mixture was stirred for 3 hours and evaporated. To a suspension of the residue in dichloromethane was added a solution of 1,3-cyclohexanedione (1.52 g) in dichloromethane and triethylamine (4.16 g) dropwise at 0° C. The reaction mixture was warmed to 20° C., stirred for 0.5 hour, diluted (ethyl acetate) and washed with aqueous citric acid. The organic layer was dried (magnesium sulfate), evaporated and the residue purified by chromatography to give 3-[4-(1,2,4-triazol-1-yl)-2-trifluoromethylbenzoyloxy]cyclohex-2-en- 1-one as a yellow solid (3.05 g), NMR 2.15(m,2H), 2.50(t,2H), 2.70(t, 2H), 6.10(s,1 H), 8.03(m,1H), 8.12(d,1H), 8.19(s,1H), 8.22 (s,1H), 8.73(s,1H).

By proceeding in a similar manner the following compounds were also prepared:

5,5-dimethyl-3-[4-(1,2,4-triazol-1-yl)-2-trifluoromethylbenzoyloxy]cyclohex-2-en-1-one, which was used directly in the following stage;

5-methyl-3-[4-(1,2,4-triazol-1-yl)-2-trifluoromethylbenzoyloxy]cyclohex-2-en-1-one, NMR 1.17 (d, 3H), 2.15–2.30 (m, 2H), 2.35–2.75 (m, 3H), 6.08 (s, 1H), 8.00–8.27 (m, 4H), 8.78 (s, 1H); 5,5-dimethyl-3-[2-chloro-4-(1,2,4-triazol-1-yl)benzoyloxy]cyclohex-2-en-1-one, NMR 1.18 (s, 6H), 2.35 (s, 2H), 2.60 (s, 2H), 6.08 (s, 1H), 7.75 (d, 1H), 7.97 (s, 1H), 8.10–8.20 (m, 2H), 8.76 (s, 1H);

3-[2-chloro-4-(1,2,4-triazol-1-yl)benzoyloxy]cyclohex-2-en-1-one; 5-methyl-3-[2-chloro-4-(1,2,4-triazol-1-yl) benzoyloxy]cyclohex-2-en-1-one;

3-[2-methylthio-4-(1,2,4-triazol-1-yl)benzoyloxy] cyclohex-2-en-1-one; and

3-[2-methyl-4-(1,2,4-triazol-1-yl)benzoyloxy]cyclohex-2-en-1-one.

Reference Example 2

To a solution of methyl 4-(1,2,4-triazol-1-yl)-2-trifluoromethylbenzoate (5.07 g) in methanol was added aqueous sodium hydroxide (1.50 g) at 20° C. The mixture was stirred for 4 hours, partially evaporated and extracted with ether. The aqueous layer was acidified (aqueous citric acid) and extracted with ethyl acetate. The organic layer was dried (magnesium sulfate), and evaporated to give 4-(1,2,4-triazol-1-yl)-2-trifluoromethylbenzoic acid (3.32 g), NMR 8.25(1H), 8.34–8.42(3H), 10.00(s, 1H).

By proceeding in a similar manner the following compounds were also prepared:

2-chloro-4-(1,2,4-triazol-1-yl)benzoic acid, NMR 7.71 (d, 1H), 7.93 (s, 1H), 8.05–8.18 (m, 1H), 8.82 (s, 1H);

2-methylthio-4-(1,2,4-triazol-1-yl)benzoic acid, NMR 2.5 (s,3H), 7.7(m,2H), 8.0(d,1H), 8.3(s,1H), 9.5(s,1H), 13.2(bs, 1H); and 2-methyl-4-(1,2,4-triazol-1-yl)benzoic acid, NMR 2.6(s,3H), 7.8(d,1H), 7.9(s,1H), 8.0(d,1H), 8.3(s,1H), 9.4(s, 1H), 13.0(bs,1H).

Reference Example 3

To a solution of methyl 4-fluoro-2-trifluoromethylbenzoate (4.95 g) in N,N-dimethylformamide was added 1,2,4-triazole (2.0 g) and potassium carbonate (4.0 g) at 20° C. and the mixture stirred for 4 hours at 60° C. The mixture was diluted (ether), washed (aqueous citric acid) and dried (magnesium sulfate). The residue was purified by chromatography to give methyl 4-(1,2,4-triazol-1-yl)-2-trifluoromethylbenzoate (5.07 g), NMR 3.98(s,3H),7.94–8.05(2H),8.15(2H),8.71 (s,1H).

By proceeding in a similar manner the following compounds were also prepared:

methyl 2-chloro-4-(1,2,4-triazol-1-yl)benzoate, NMR 3.97 (s, 3 H), 7.68 (d, 1H), 7.89 (s, 1H), 8.02 (s, 1H), 8.14 (s, 1H), 8.70 (s, 1H);

methyl 2-methylthio-4-(1,2,4-triazol-1-yl)benzoate, mp 155–156° C.; and methyl 2-methyl-4-(1,2,4-triazol-1-yl)benzoate, mp 106–107° C.

According to a feature of the present invention, there is provided a method for controlling the growth of weeds (i.e. undesired vegetation) at a locus which comprises applying to the locus a herbicidally effective amount of at least one 2-benzoylcyclohexane-1,3-dione derivative of formula (I) or an agriculturally acceptable salt or metal complex thereof. For this purpose, the 2-benzoylcyclohexane-1,3-dione derivatives are normally used in the form of herbicidal compositions (i.e. in association with compatible diluents or carriers and/or surface active agents suitable for use in herbicidal compositions), for example as hereinafter described.

The compounds of formula (I) show herbicidal activity against dicotyledonous (i.e. broad-leafed) and monocotyledonous (i.e. grass) weeds by pre- and/or post-emergence application.

By the term "pre-emergence application" is meant application to the soil in which the weed seeds or seedlings are present before emergence of the weeds above the surface of the soil. By the term "post-emergence application" is meant application to the aerial or exposed portions of the weeds which have emerged above the surface of the soil.

For example, the compounds of formula (I) may be used to control the growth of:

broad-leafed weeds, for example, *Abutilon theophrasti, Amaranthus retroflexus, Bidens vilosa, Chenopodium album, Galium aparine*, Ipomoea spp. e.g. *Ipomoea Durnurea, Sesbania exaltata, Sinapis arvensis, Solanum nigrum* and *Xanthium strumarium*, and grass weeds, for example *Alopecurus myosuroides, Avena fatua, Digitaria sanguinalis, Echinochloa crus-galli, Sor-* ghum bicolor, Eleusine indica and Setaria spp, e.g. *Setaria faberii* or *Setaria viridis*, and sedges, for example, *Cyperus esculentus*.

The amounts of compounds of formula (I) applied vary with the nature of the weeds, the compositions used, the time of application, the climatic and edaphic conditions and (when used to control the growth of weeds in crop-growing areas) the nature of the crops. When applied to a crop-growing area, the rate of application should be sufficient to control the growth of weeds without causing substantial permanent damage to the crop. In general, taking these factors into account, application rates from 0.01 kg to 2 kg of active material per hectare give good results. However, it is to be understood that higher or lower application rates may be used, depending upon the particular problem of weed control encountered.

The compounds of formula (I) may be used to control selectively the growth of weeds, for example to control the growth of those species hereinbefore mentioned, by pre- or post-emergence application in a directional or non-directional fashion, e.g. by directional or non-directional spraying, to a locus of weed infestation which is an area used, or to be used, for growing crops, for example cereals, e.g. wheat, barley, oats, maize and rice, soya beans, field and dwarf beans, peas, lucerne, cotton, peanuts, flax, onions, carrots, cabbage, oilseed rape, sunflower, sugar beet, and permanent or sown grassland before or after sowing of the crop or before or after emergence of the crop. For the selective control of weeds at a locus of weed infestation which is an area used, or to be used, for growing of crops, e.g. the crops hereinbefore mentioned, application rates from 0.01 kg to 1.0 kg, and preferably from 0.025 kg to 0.25 kg, of active material per hectare are particularly suitable.

The compounds of formula (I) may also be used to control the growth of weeds, especially those indicated above, by pre- or post-emergence application in established orchards and other tree-growing areas, for example forests, woods and parks, and plantations, e.g. sugar cane, oil palm and rubber plantations. For this purpose they may be applied in a directional or non-directional fashion (e.g. by directional or non-directional spraying) to the weeds or to the soil in which they are expected to appear, before or after planting of the trees or plantations at application rates from 0.25 kg to 2.0 kg, and preferably from 0.25 kg to 1.0 kg of active material per hectare.

The compounds of formula (I) may also be used to control the growth of weeds, especially those indicated above, at loci which are not crop-growing areas but in which the control of weeds is nevertheless desirable.

Examples of such non-crop-growing areas include airfields, industrial sites, railways, roadside verges, the verges of rivers, irrigation and other waterways, scrublands and fallow or uncultivated land, in particular where it is desired to control the growth of weeds in order to reduce fire risks. When used for such purposes in which a total herbicidal effect is frequently desired, the active compounds are normally applied at dosage rates higher than those used in crop-growing areas as hereinbefore described. The precise dosage will depend upon the nature of the vegetation treated and the effect sought.

Pre- or post-emergence application, and preferably pre-emergence application, in a directional or non-directional fashion (e.g. by directional or non-directional spraying) at application rates from 0.5 kg to 2.0 kg, and preferably from 0.5 kg to 1.0 kg, of active material per hectare are particularly suitable for this purpose.

When used to control the growth of weeds by pre-emergence application, the compounds of formula (I) may be incorporated into the soil in which the weeds are expected to emerge. It will be appreciated that when the compounds of formula (I) are used to control the growth of weeds by post-emergence application, i.e. by application to the aerial or exposed portions of emerged weeds, the compounds of formula (I) will also normally come into contact with the soil and may also then exercise a pre-emergence control on later-germinating weeds in the soil.

Where especially prolonged weed control is required, the application of the compounds of formula (I) may be repeated if required. According to a further feature of the present invention, there are provided compositions suitable for herbicidal use comprising one or more of the 2-benzoylcyclohexane-1,3-dione derivatives of formula (I) or an agriculturally acceptable salt or metal complex thereof, in association with, and preferably homogeneously dispersed in, one or more compatible agriculturally-acceptable diluents or carriers and/or surface active agents [i.e. diluents or carriers and/or surface active agents of the type generally accepted in the art as being suitable for use in herbicidal compositions and which are compatible with compounds of formula (I)]. The term "homogeneously dispersed" is used to include compositions in which the compounds of formula (I) are dissolved in other components. The term "herbicidal compositions" is used in a broad sense to include not only compositions which are ready for use as herbicides but also concentrates which must be diluted before use. Preferably, the compositions contain from 0.05 to 90% by weight of one or more compounds of formula (I).

The herbicidal compositions may contain both a diluent or carrier and surface-active (e.g. wetting, dispersing, or emulsifying) agent.

Surface-active agents which may be present in herbicidal compositions of the present invention may be of the ionic or non-ionic types, for example sulphoricinoleates, quaternary ammonium derivatives, products based on condensates of ethylene oxide with alkyl and polyaryl phenols. e.g. nonyl- or octyl-phenols, or carboxylic acid esters of anhydrosorbitols which have been rendered soluble by etherification of the free hydroxy groups by condensation with ethylene oxide, alkali and alkaline earth metal salts of sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates and sodium and calcium alkylbenzene sulphonates.

Suitably, the herbicidal compositions according to the present invention may comprise up to 10% by weight, e.g. from 0.05% to 10% by weight, of surface-active agent but, if desired, herbicidal compositions according to the present invention may comprise higher proportions of surface-active agent, for example up to 15% by weight in liquid emulsifiable suspension concentrates and up to 25% by weight in liquid water soluble concentrates.

Examples of suitable solid diluents or carriers are aluminium silicate, talc, calcined magnesia, kieselguhr, tricalcium phosphate, powdered cork, absorbent carbon black and clays such as kaolin and bentonite. The solid compositions (which may take the form of dusts, granules or wettable powders) are preferably prepared by grinding the compounds of formula (I) with solid diluents or by impregnating the solid diluents or carriers with solutions of the compounds of formula (I) in volatile solvents, evaporating the solvents and, if necessary, grinding the products so as to obtain powders. Granular formulations may be prepared by absorbing the compounds of formula (I) (dissolved in suitable solvents, which may, if desired, be volatile) onto the solid diluents or carriers in granular form and, if desired, evaporating the solvents, or by granulating compositions in powder form obtained as described above. Solid herbicidal compositions, particularly wettable powders and granules, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, glycols, tetrahydrofurfuryl alcohol, acetophenone, cyclohexanone, isophorone, toluene, xylene, mineral, animal and vegetable oils and light aromatic and naphthenic fractions of petroleum (and mixtures of these diluents). Surface-active agents, which may be present in the liquid compositions, may be ionic or non-ionic (for example of the types described above) and may, when liquid, also serve as diluents or carriers.

Powders, dispersible granules and liquid compositions in the form of concentrates may be diluted with water or other suitable diluents, for example mineral or vegetable oils, particularly in the case of liquid concentrates in which the diluent or carrier is an oil, to give compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, spreading agents, stabilisers, sequestering agents, anti-caking agents, colouring agents and corrosion inhibitors. These adjuvants may also serve as carriers or diluents.

Herbicidal compositions according to the present invention may also comprise the compounds of formula I in association with, and preferably homogeneously dispersed in, one or more other pesticidally active compounds and, if desired, one or more compatible pesticidally acceptable diluents or carriers, surface-active agents and conventional adjuvants as hereinbefore described.

Examples of other pesticidally active compounds which may be included in, or used in conjunction with, the herbicidal compositions of the present invention include herbicides, for example to increase the range of weed species controlled for example alachlor [2-chloro-2,6'-diethyl-N-(methoxy-methyl)-acetanilide], atrazine [2-chloro-4-ethylamino-6-isopropylamino-1,3,5-triazine], bromoxynil [3,5-dibromo-4-hydroxybenzonitrile], chlortoluron [N'-(3-chloro-4-methylphenyl)-N,N-dimethylurea], cyanazine [2-chloro-4-(1-cyano-1-methylethylamino)-6-ethylamino-1,3,5-triazine], 2,4-D [2,4-dichlorophenoxyacetic acid], dicamba [3,6-dichloro-2-methoxybenzoic acid], difenzoquat [1,2- dimethyl-3 ,5-diphenyl-pyrazolium salts], flampropmethyl [methyl N-2-(N- benzoyl-3-chloro-4-fluoroanilino)-propionate], fluometuron [N'-(3-trifluoromethylphenyl)-N,N-dimethylurea], isoproturon [N'-(4-isopropylphenyl)-N,N-dimethylurea], insecticides, e.g. synthetic pyrethroids, e.g permethrin and cypermethrin, and fungicides, e.g. carbamates, e.g. methyl N-(1-butyl-carbamoyl-benzimidazol-2-yl)carbamate, and triazoles e.g. 1-(4-chloro-phenoxy)-3,3-dimethyl-1-(1,2,4-triazol-1-yl)-butan-2-one.

Pesticidally active compounds and other biologically active materials which may be included in, or used in conjunction with, the herbicidal compositions of the present invention, for example those hereinbefore mentioned, and which are acids, may, if desired, be utilised in the form of conventional derivatives, for example alkali metal and amine salts and esters.

The following Examples illustrate herbicidal compositions according to the present invention. The following trade marks appear in the Examples: Synperonic, Solvesso, Arylan, Arkopon, Sopropon, Tixosil, Soprophor, Attagel, Rhodorsil.

EXAMPLE C1

An emulsifiable concentrate is formed from:

| | |
|---|---|
| Active ingredient (Compound 1) | 20% w/v |
| N-Methylpyrrolidinone (NMP) | 25% w/v |
| Calcium dodecylbenzenesulphonate (70%) (CaDDBS) (Arylan CA) | 4% w/v |
| Nonylphenol ethylene oxide propylene oxide condensate (NPEOPO) (Synperonic NPE 1800) | 6% w/v |
| Aromatic solvent (Solvesso) | to 100 volumes | by stirring NMP, active ingredient (Compound 1), CaDDBS, NPEOPO and Aromatic solvent until a clear solution is formed, and adjusting to volume with Aromatic solvent.

EXAMPLE C2

A wettable powder is formed from:

| | |
|---|---|
| Active ingredient (Compound 1) | 50% w/w |
| Sodium dodecylbenzenesulphonate (Arylan SX85) | 3% w/w |
| Sodium methyl oleoyl taurate (Arkopon T) | 5% w/w |
| Sodium polycarboxylate (Sopropon T36) | 1% w/w |
| Microfine silicon dioxide (Tixosil 38) | 3% w/w |
| China clay | 38% w/w | by blending the above ingredients together and grinding the mixture in an air jet mill.

EXAMPLE C3

A suspension concentrate is formed from:

| | |
|---|---|
| Active ingredient (Compound 1) | 50% w/v |
| Antifreeze (Propylene glycol) | 5% w/v |
| Ethoxylated tristyrylphenol phosphate (Soprophor FL) | 0.5% w/v |
| Nonyl phenol 9 mole ethoxylate (Ethylan BCP) | 0.5% w/v |
| Sodium polycarboxylate (Sopropon T36) | 0.2% w/v |
| Attaclay (Attagel) | 1.5% w/v |
| Antifoam (Rhodorsil AF426R) | 0.003% w/v |
| Water | to 100 volumes | by stirring the above ingredients together and milling in a bead mill.

EXAMPLE C4

A water dispersible granule is formed from:

| | |
|---|---|
| Active ingredient (Compound 1) | 50% w/w |
| Sodium dodecylbenzenesulphonate (Arylan SX 85) | 3% w/w |
| Sodium methyl oleoyl taurate (Arkopon T) | 5% w/w |
| Sodium polycarboxylate (Sopropon T36) | 1% w/w |
| Binder (Sodium lignosulphonate) | 8% w/w |
| China clay | 30% w/w |
| Microfine silicon dioxide (Tixosil 38) | 3% w/w | by blending the above ingredients together, grinding the mixture in an air jet mill and granulating by addition of water in a suitable granulation plant (e.g. fluid bed drier) and drying. Optionally the active ingredient may be ground either on its own or admixed with some or all of the other ingredients.

The compounds of the invention have been used in herbicidal applications according to the following procedures.

Method of Use of Herbicidal Compounds
Test Method A
a) General

Appropriate quantities of the compounds used to treat the plants were dissolved in acetone to give solutions equivalent to application rates of up to 250 g test compound per hectare (g/ha). These solutions were applied from a standard laboratory herbicide sprayer delivering the equivalent of 290 liters of spray fluid per hectare.

b) Weed control: Pre-emergence

The seeds were sown in 70 mm square, 75 mm deep plastic pots in non-sterile soil. The quantities of seed per pot were as follows:

| Weed species | Approx number of seeds/pot |
|---|---|
| 1) Broad-leafed weeds | |
| Abutilon theophrasti | 10 |
| Amaranthus retroflexus | 20 |
| Galium aparine | 10 |
| Ipomoea purpurea | 10 |
| Xanthium strumarium | 2 |
| 2) Grass weeds | |
| Alopecurus myosuroides | 15 |
| Avena fatua | 10 |
| Echinochloa crus-galli | 15 |
| Setaria viridis | 20 |
| 3) Sedges | |
| Cyperus esculentus | 3 |
| Crop | |
| 1) Broad-leafed | |
| Cotton | 3 |
| Soya | 3 |
| 2) Grass | |
| Maize | 2 |
| Rice | 6 |
| Wheat | 6 |

The compounds of the invention were applied to the soil surface, containing the seeds, as described in (a). A single pot of each crop and each weed was allocated to each treatment, with unsprayed controls and controls sprayed with acetone alone.

After treatment the pots were placed on capillary matting kept in a glass house, and watered overhead. Visual assessment of crop damage was made 20–24 days after spraying. The results were expressed as the percentage reduction in growth or damage to the crop or weeds, in comparison with the plants in the control pots.

c) Weed control: Post-emergence

The weeds and crops were sown directly into John Innes potting compost in 75 mm deep. 70 mm square pots except for Amaranthus which was pricked out at the seedling stage and transferred to the pots one week before spraying. The plants were then grown in the greenhouse until ready for spraying with the compounds used to treat the plants. The number of plants per pot were as follows:

1) Broad Leafed Weeds

| Weed species | Number of plants per root | Growth stage |
|---|---|---|
| Abutilon theophrasti | 3 | 1–2 leaves |
| Amaranthus retroflexus | 4 | 1–2 leaves |
| Galium aparine | 3 | 1st whorl |
| Ipomoea purpurea | 3 | 1–2 leaves |
| Xanthium strumarium | 1 | 2–3 leaves |

2) Grass Weeds

| Weed species | Number of plants per root | Growth stage |
|---|---|---|
| Alopecurus myosuroides | 8–12 | 1–2 leaves |
| Avena fatua | 12–18 | 1–2 leaves |
| Echinochloa crus-galli | 4 | 2–3 leaves |
| Setaria viridis | 15–25 | 1–2 leaves. |

3) Sedges

| Weed species | Number of plants per root | Growth stage |
|---|---|---|
| Cyperus esculentus | 3 | 3 leaves. |

1) Broad Leafed

| Crops | Number of plants per root | Growth stage |
|---|---|---|
| Cotton | 2 | 1 leaf |
| Soya | 2 | 2 leaves. |

2)Grass

| Crops | Number of plants per root | Growth stage |
|---|---|---|
| Maize | 2 | 2–3 leaves |
| Rice | 4 | 2–3 leaves |
| Wheat | 5 | 2–3 leaves. |

The compounds used to treat the plants were applied to the plants as described in (a). A single pot of each crop and weed species was allocated to each treatment, with unsprayed controls and controls sprayed with acetone alone.

After treatment the pots were placed on capillary matting in a glass house, and watered overhead once after 24 hours and then by controlled sub-irrigation. Visual assessment of crop damage and weed control was made 20–24 days after spraying. The results were expressed as the percentage reduction in growth or damage to the crop or weeds, in comparison with the plants in the control pots.

Test Method B

Paddy Post-Emergence Application in Greenhouse

Paddy field soil was filled in 170 cm² plastic pots, a suitable amount of water and chemical fertilisers were added thereto and kneaded to convert it to a state of a paddy.

Paddy rice plants (variety; Koshihikari), that had been grown in advance in a greenhouse to a stage of two leaves, were transplanted to each pot (two seedlings per pot). Then in each pot there were sown predetermined amounts of seeds of *Echinochloa oryzicola, Monochoria vaginalis, Lindemia procumbens* and *Scirpus juncoides* respectively, and water was added to a depth of 3 cm.

After having grown the plants in a greenhouse until *Echinochloa oryzicola* reached a stage of 1.5 leaves, solutions were prepared in 100% acetone using compounds described in the Examples so that they contained active ingredients in an amount equivalent to 75, 300 and 1200 g/ha. The solutions were applied by dropping with a pipette.

After 21 days from the application with the chemicals, herbicidal effects on each weed and phytotoxicity on paddy rice plants were visually assessed, and the results expressed as the percentage reduction in growth or damage to the crop or weeds in comparison with the plants in the control pots.

When applied pre- or post-emergence in Test Method A at 250 g/ha or less compounds 1, 3, 32, 42, 99 and 166 of the invention gave at least 90% reduction in growth of one or more of the weed species; at levels of application toxic to the weeds this compound was selective in at least one of the crop species.

When applied at 1200 g/ha or less, in Test Method B, compounds 1–3 , 1, 88, 99 and 166 of the invention (Tave at least 90° reduction in growth of one or more of the weed species listed above.

While the invention has been described in terms of various preferred embodiments, the person skilled in the art will appreciate that various modifications, substitutions, omissions and changes can be made without departing from the spirit thereof. Accordingly, it is intended that the scope of the present invention be limited solely by the scope of the following claims, including equivalents thereof.

What is claimed is:

1. A compound having the formula:

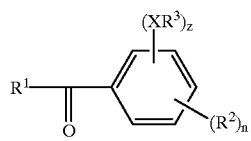

wherein:

$R^1$ represents a group of formula (II), (III), IV) or (V):

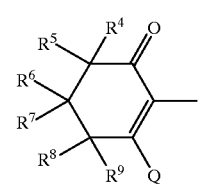

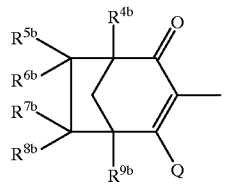

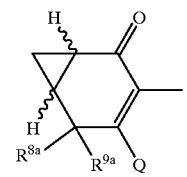

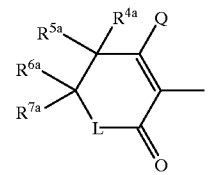

or a corresponding formula (IVa) or (Va):

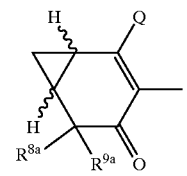

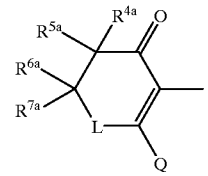

in which the position of the carbonyl group and the group Q are reversed and the double bond in the ring is attached to the carbon atom attached to the group Q;

$R^2$ represents:

halogen;

lower alkyl which is unsubstituted or is substituted by one or more halogen or —$OR^{10}$;

cycloalkyl having from three to six carbon atoms; or nitro, cyano, —$CO_2R^{10}$, —$NR^{10}R^{11}$, —$S(O)_pR^{12}$, —$O(CH_2)_mOR^{10}$, —$COR^{10}$, —$N(R^{13})SO_2R^{12}$, —$OR^{12}$, —OH, —$OSO_2R^{12}$, (—$CR^{14}R^{15})_rS(O)_q R^{12}$, —$CONR^{10}R^{11}$, —$N(R^{13})$—$C(Z)$=Y, —$C(R^{14}R^{15})NR^{13}R^{16}$, —$CH_2P(O)R^{10a}R^{10b}$, $R^{17}$, $SF_5$, or benzyl which is unsubstituted or is substituted by from one to five $R^{18}$ which are the same or different;

or two groups $R^2$, together with adjacent carbon atoms of the phenyl ring, form a second phenyl ring or a 5- or 6-membered saturated or unsaturated heterocyclic ring which is fused to the first ring and has one or two oxygen or sulfur ring atoms and is unsubstituted or substituted by one or more halogen, lower alkyl, lower haloalkyl or lower alkoxy, or one of the ring carbon atoms of the heterocyclic ring forms part of a carbonyl group or an oxime or lower alkoxyimine thereof;

n represents zero or an integer from one to three; when n is greater than one, the groups $R^2$ are the same or different;

m represents one, two or three;

p and q represent zero, one or two;

t represents one, two, three of four; when t is more than one, $R^{14}$ and $R^{15}$ are the same or different;

X represents —$(CR^{14}R^{15})_v$—;

v represents zero or one;

$R^3$ represents a 5-membered heteroaromatic ring of formula (VI):

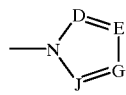

(VI)

in which D, E, G and J independently represent $CR^{19}$ or a nitrogen atom, with at least one of D, E, G and J representing $CR^{19}$, each $CR^{19}$ when more than one is present being the same or different; or two adjacent groups form a phenyl or a 5- to 7-membered heteroaromatic ring which is fused to the first ring and is unsubstituted or substituted by one or more $R^{20}$, the 5- to 7-membered heterocyclic ring having from one to four heteroatoms in the ring which are the same or different and which are nitrogen, oxygen or sulfur;

z represents one or two; when z represents two, the —$XR^3$ groups are the same or different;

Q represents hydroxy, lower alkoxy, $OR^{21}$, $SR^{21}$ or $SR^{22}$;

L represents oxygen or $NR^{14}$;

$R^4$, $R^{4a}$, $R^{4b}$, $R^5$, $R^{5a}$, $R^{5b}$, $R^6$, $R^{6a}$, $R^{6b}$, $R^7$, $R^{7a}$, $R^{7b}$, $R^8$, $R^{8a}$, $R^{8b}$, $R^9$, $R^{9a}$ and $R^{9b}$ represent the same or different members selected from the group consisting of hydrogen, $R^{17}$, —$(CH_2)_uCO_2R^{14}$, halogen, cyano, lower alkoxy, —$(CH_2)_x$-phenyl wherein phenyl is unsubstituted or is substituted by from one to five $R^{18}$ which are the same or different, and cycloalkyl having from three to six carbon atoms and being unsubstituted or substituted by lower alkyl or —$S(O)_pR^{22}$;

u represents zero, one or two;

x represents zero or one;

each of $R^{10}$ and $R^{11}$, which are the same or different, represents hydrogen or $R^{17}$;

each of $R^{10a}$ and $R^{10b}$, which are the same or different, represents lower alkyl or lower alkoxy;

$R^{12}$ represents:
$R^{17}$;
cycloalkyl having from three to six carbon atoms; or
—$(CH_2)_w$-phenyl wherein phenyl is unsubstituted or is substituted by from one to five $R^{18}$ which are the same or different;

w represents zero or one;

$R^{13}$ represents $R^{12}$ or $OR^{22}$;

$R^{14}$ and $R^{15}$ independently represent hydrogen, lower alkyl or lower haloalkyl;

$R^{16}$ represents —$SO_2R^{12}$ or —$C(Z)=Y$;

$R^{17}$ represents lower alkyl, lower haloalkyl, lower alkenyl, lower haloalkenyl, lower alkynyl or lower haloalkynyl;

$R^{18}$ represents halogen, $R^{23}$, nitro, cyano, —$CO_2R^{10}$, —$S(O)_pR^{22}$, —$OR^{22}$ or —$NR^{10}R^{11}$;

$R^{19}$ represents hydrogen, halogen, $R^{23}$, nitro, cyano, —$CO_2R^{10}$, —$S(O)_pR^{22}$, —$OR^{22}$, —$NR^{10}R^{11}$ or cyclopropyl;

$R^{20}$ represents halogen or $R^{17}$;

$R^{21}$ represents phenyl which is unsubstituted or is substituted by from one to five members selected from the group consisting of halogen, lower alkyl, lower haloalkyl, lower alkoxy and nitro;

$R^{22}$ represents lower alkyl or lower haloalkyl;

$R^{23}$ represents straight- or branched-chain alkyl having one to three carbon atoms, which is unsubstituted or is substituted by one or more halogen atoms;

Y is oxygen or sulfur;

Z represents $R^{17}$, —$NR^{24}R^{25}$, —$SR^{12}$ or —$OR^{12}$; and $R^{24}$ and $R^{25}$ independently represent hydrogen or $R^{12}$;

or an agriculturally acceptable salt or metal complex thereof.

2. A compound according to claim 1, wherein two groups $R^2$; together with adjacent carbon atoms of the phenyl ring, form a 5- or 6-membered saturated or unsaturated heterocyclic ring fused to the first ring, the resultant fused ring system, which is unsubstituted or substituted, being a thiochroman, chroman, 2H-thiochromene, 2H-chromene, 4H-thiochromene, 4H-chromene, isothiochroman, isochroman, isothiochromene, isochromene, 1,3-benzodithiole, 1,3-benzodioxole, 1,3-benzoxathiole, 1,4-benzodithiin, 1,4-benzoxathiin, 1,4-benzoxathian, 1,3-benzoxathian, 3,1-benzoxathian or 1,3-benzodithian ring system.

3. A compound according to claim 1, wherein t is one.

4. A compound according to claim 1, wherein $R^{14}$ and $R^{15}$ independently represent hydrogen, $C_1$–$C_3$ alkyl or $C_1$–$C_3$ haloalkyl.

5. A compound according to claim 1, wherein Y is oxygen.

6. A compound according to claim 1, wherein one $XR^3$ group is present.

7. A compound according to claim 6, wherein the $XR^3$ group is in the 2- or 4-position of the phenyl ring.

8. A compound according to claim 1, wherein X represents —$(CR^{14}R^{15})_v$— wherein v represents zero.

9. A compound according to claim 1, wherein Q represents hydroxy.

10. A compound according to claim 1, wherein Q represents S-phenyl.

11. A compound according to claim 1, wherein $R^3$ represents pyrazol-1-yl, imidazol-1-yl, 1,2,4-triazol-1-yl, 1,2,3-triazol-1-yl, 1,2,3-triazol-2-yl, 1,2,3,4-tetrazol-1-yl or benzimidazol-1-yl, each of which is substituted by one or two $R^{19}$ groups, which are the same or different.

12. A compound according to claim 2, wherein $R^3$ represents pyrazol-1-yl, imidazol-1-yl, 1,2,4-triazol-1-yl, 1,2,3-triazol-1-yl, 1,2,3-triazol-2-yl, 1,2,3,4-tetrazol-1-yl or benzimidazol-1-yl, each of which is substituted by one or two $R^{19}$ groups, which are the same or different.

13. A compound according to claim 1, wherein $R^3$ is a ring of formula (VI) wherein $R^{19}$ represents hydrogen, halogen or $R^{23}$.

14. A compound according to claim 1, wherein $R^1$ represents a group of formula (II).

15. A compound according to claim 2, wherein $R^1$ represents a group of formula (II).

16. A compound according to claim 14, wherein one $XR^3$ group is present.

17. A compound according to claim 16, wherein the $XR^3$ group is in the 2- or 4-position of the phenyl ring.

18. A compound according to claim 14, wherein Q represents hydroxy.

19. A compound according to claim 14, wherein $R^3$ represents pyrazol-1-yl, imidazol-1-yl, 1,2,4-triazol-1-yl, 1,2,3-triazol-1-yl, 1,2,3-triazol-2-yl, 1,2,3,4-tetrazol-1-yl or benzimidazol-1-yl, each of which is substituted by one or two $R^{19}$ groups, which are the same or different.

20. A compound according to claim 1, wherein $R^2$ represents halogen; straight- or branched-chain alkyl having up to four carbon atoms which is unsubstituted or substituted by one or more halogen atoms; nitro; cyano; $—S(O)_pR^{12}$; $—OR^{12}$; $—CH_2S(O)_qR^{12}$ wherein $R^{12}$ represents lower alkyl or lower haloalkyl; or benzyl which is unsubstituted or substituted by $—S(O)_pR^{22}$ wherein $R^{22}$ represents lower alkyl; or two groups $R^2$ together with adjacent carbon atoms of the phenyl ring form a second phenyl ring.

21. A compound according to claim 20, wherein $R^1$ represents a group of formula (II).

22. A compound according to claim 21, wherein one $XR^3$ group is present.

23. A compound according to claim 22, wherein the $XR^3$ group is in the 2- or 4-position of the phenyl ring.

24. A compound according to claim 21, wherein Q represents hydroxy.

25. A compound according to claim 21, wherein $R^3$ represents pyrazol-1-yl, imidazol-1-yl, 1,2,4-triazol-1-yl, 1,2,3-triazol-1-yl, 1,2,3-triazol-2-yl, 1,2,3,4-tetrazol-1-yl or benzimidazol-1-yl, each of which is substituted by one or two $R^{19}$ groups, which are the same or different.

26. A compound according to claim 1, wherein:

$R^1$ represents:
a group of formula (II) wherein $R^4$, $R^5$, $R^6$, $R^7$, $R^8$, and $R^9$ represent hydrogen or lower alkyl;
a group of formula (III) wherein $R^{4b}$, $R^{5b}$, $R^{6b}$, $R^{7b}$, $R^{8b}$ and $R^{9b}$ represent hydrogen or lower alkyl;
a group of formula (IV) wherein $R^{8a}$ and $R^{9a}$ represent hydrogen or lower alkyl; or
a group of formula (V) wherein $R^{4a}$, $R^{5a}$, $R^{6a}$ and $R^{7a}$ represent hydrogen or lower alkyl, and L represents NH;

Q represents hydroxy or —S-phenyl;

$R^2$ represents:
straight- or branched-chain alkyl having up to three carbon atoms, which is unsubstituted or substituted by one or more halogen atoms; or
halogen, nitro, $—S(O)_pR^{12}$, $—OR^{12}$, $—CH_2S(O)_qR^{12}$, $—CH_2NR^{13}R^{16}$, $—N(R^{13})SO_2R^{12}$, $—N(R^{13})CO_2R^{12}$ or benzyl which is unsubstituted or substituted by $—S(O)_pR^{22}$;

n represents zero, one or two;

X represents $—(CH_2)_y—$;

$R^3$ represents pyrazol-1-yl, imidazol-1-yl, 1,2,4-triazol-1-yl, 1,2,3-triazol-1-yl, 1,2,3-triazol-2-yl, 1,2,3,4-tetrazol-1-yl or benzimidazol-1-yl, each of which is substituted by one or two $R^{19}$ groups;

z represents one;

$R^{12}$ and $R^{13}$ independently represent lower alkyl or lower haloalkyl;

$R^{16}$ represents $—SO_2R^{12}$ or $CO_2R^{12}$;

$R^{19}$ represents hydrogen or straight- or branched-chain alkyl having up to three carbon atoms; and $R^{22}$ represents lower alkyl.

27. A compound according to claim 26, wherein $R^1$ represents a group of formula (II).

28. A compound according to claim 27, wherein:

$R^1$ represents a group of formula (II) wherein $R^4$, $R^5$, $R^6$, $R^7$, $R^8$ and $R^9$ represent hydrogen, methyl or ethyl;

Q represents hydroxy or —S-phenyl;

$R^2$ represents:
halogen, straight- or branched-chain alkyl, having up to three carbon atoms which is unsubstituted or substituted by one or more halogen atoms; $—S(O)_pCH_3$; $—CH_2S(O)_qCH_3$; $—OCH_3$; or benzyl which is unsubstituted or substituted by $—S(O)_pCH_3$;

X represents a bond;

$R^3$ represents pyrazol-1-yl, imidazol-1-yl, 1,2,3-triazol-1-yl, 1,2,3-triazol-2-yl, 1,2,4-triazol-1-yl or 1,2,3,4-tetrazol-1-yl, each of which has one or two $R^{19}$ substituents, wherein $R^{19}$ represents hydrogen, halogen, methyl or halogenated methyl;

z represents one; and n represents 0, 1 or 2.

29. The compound according to claim 1, which is:

(a) 2-[4-(1,2,4-triazol-1-yl)-2-trifluoromethylbenzoyl]cyclohexane-1,3-dione;

(b) 3-phenylthio-2-[4-(1,2,4-triazol-1-yl)-2-trifluoromethylbenzoyl]cyclohex-2-ene-1-one;

(c) 5,5-dimethyl-2-[4-(1,2,4-triazol-1-yl)-2-trifluoromethylbenzoyl]cyclohexane-1,3-dione;

(d) 2-[2-chloro-4-(1,2,4-triazol-1-yl)benzoyl]cyclohexane-1,3-dione;

(e) 2-[2-methyl-4-(1,2,4-triazol-1-yl)benzoyl]cyclohexane-1,3-dione;

(f) 2-[2-methylthio-4-(1,2,4-triazol-1-yl)benzoyl]cyclohexane-1,3-dione;

(g) 5-methyl-2-[4-(1,2,4-triazol-1-yl)-2-trifluoromethylbenzoyl]cyclohexane-1,3-dione;

(h) 5-methyl-2-[2-chloro-4-(1,2,4-triazol-1-yl)benzoyl]cyclohexane-1,3-dione; or (i) 5,5-dimethyl-2-[2-chloro-4-(1,2,4-triazol-1-yl)benzoyl]cyclohexane-1,3-dione.

30. A herbicidal composition comprising a herbicidally effective amount of a compound according to claim 1 or an agriculturally acceptable salt or metal complex thereof, and at least one member selected from the group consisting of an agriculturally acceptable carrier and an agriculturally acceptable surface active agent.

31. A method for the control of weeds at a locus which comprises applying to said locus a herbicidally effective amount of a compound according to claim 1 or an agriculturally acceptable salt or metal complex thereof.

32. A method according to claim 31, wherein the locus is an area used, or to be used, for the growing of crops and the compound of formula (I) or salt or metal complex thereof is applied at an application rate of from about 0.01 kg to about 1 kg/ha.

33. A method for the control of weeds at a locus which comprises applying to said locus a herbicidally effective amount of a herbicidal composition according to claim 30.

34. A method according to claim 33, wherein the locus is an area used, or to be used, for the growing of crops and the herbicidal composition is applied at an application rate of from about 0.01 kg to about 1 kg of compound of formula (I) or salt or metal complex thereof per hectare.

35. A process for the preparation of a compound of formula (I) as defined in claim 1 which comprises rearranging a compound of formula (VII), (VIII), (IX) or (X):

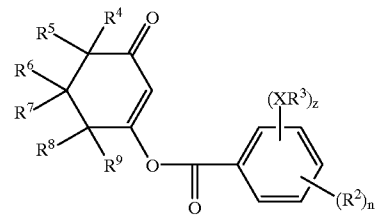
(VII)
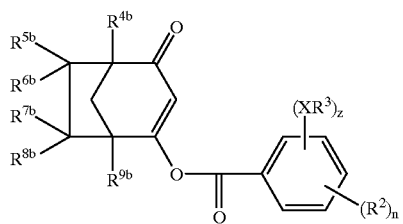
(VIII)
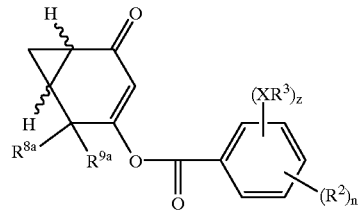
(IX)
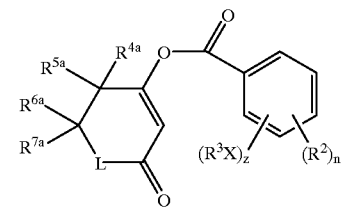
(X)
or an isomeric ester in which the position of the ring carbonyl and ester groups of formula (IX) or (X) is reversed, with a source of cyanide in the presence of a base.
* * * * *